(12) United States Patent
Wyatt et al.

(10) Patent No.: US 7,654,271 B2
(45) Date of Patent: *Feb. 2, 2010

(54) COSMETIC APPLICATOR

(75) Inventors: Peter Jonathan Wyatt, Forest Hill, MD (US); David Edward Wilson, Reisterstown, MD (US); Donald Frank Rainey, Owings Mills, MD (US)

(73) Assignee: The Procter & Gamble Company, Cincinnati, OH (US)

( * ) Notice: Subject to any disclaimer, the term of this patent is extended or adjusted under 35 U.S.C. 154(b) by 248 days.

This patent is subject to a terminal disclaimer.

(21) Appl. No.: 11/143,525

(22) Filed: Jun. 2, 2005

(65) Prior Publication Data

US 2006/0272667 A1 Dec. 7, 2006

(51) Int. Cl.
*A45D 40/26* (2006.01)
(52) U.S. Cl. ...................................... 132/218
(58) Field of Classification Search ................ 132/218, 132/309–311; 15/22.2
See application file for complete search history.

(56) References Cited

U.S. PATENT DOCUMENTS

| | | | | |
|---|---|---|---|---|
| 2,290,454 A | * | 7/1942 | Steinberg | 15/22.2 |
| 3,156,335 A | | 11/1964 | Marine | |
| 3,431,571 A | | 3/1969 | Kraus | |
| 3,661,018 A | | 5/1972 | Keefer | |
| 3,699,952 A | | 10/1972 | Waters | |
| 3,998,235 A | | 12/1976 | Kingsford | |
| 4,056,111 A | | 11/1977 | Mantelet | |
| 4,397,326 A | | 8/1983 | Formica | |
| 4,490,877 A | | 1/1985 | Drumm | |
| 4,498,490 A | | 2/1985 | Seidler | |

(Continued)

FOREIGN PATENT DOCUMENTS

DE 3833358 C2 1/1996

(Continued)

OTHER PUBLICATIONS

USPTO Office Action rejections/objections from co-pending U.S. Appl. No. 11/143,176, filed Jun. 2, 2005, Inventor: Peter Jonathan Wyatt et al., mail dates Apr. 6, 2009, Mar. 18, 2008 and Sep. 29, 2008; 28 pages.

(Continued)

*Primary Examiner*—Robyn Doan
*Assistant Examiner*—Rachel R Steitz
(74) *Attorney, Agent, or Firm*—Megan C. Hymore; Vladimir Vitenberg; S. Robert Chuey

(57) ABSTRACT

An apparatus for applying a cosmetic, such as mascara to eyelashes, includes a handle, a stem, and an applicator head coupled to the stem and supported for movement relative to the handle in a direction substantially parallel to the stem axis. An actuator moves the applicator head in an axial motion comprising a forward stroke and a reverse stroke. Additionally or alternatively, the actuator may move the applicator head in a composite motion including an axial component substantially parallel to the stem axis and having a forward stroke and a reverse stroke, and a rotational oscillating component. The actuator may be a motor having a rotating motor shaft, and the applicator may further include a transmission coupling disposed between the motor shaft and the applicator head for automatically converting rotation of the motor shaft in one direction into axially reciprocating movement of the applicator head.

16 Claims, 38 Drawing Sheets

U.S. PATENT DOCUMENTS

| | | | |
|---|---|---|---|
| 4,632,136 | A | 12/1986 | Kingsford |
| 4,687,364 | A | 8/1987 | Kingsford |
| 4,691,720 | A | 9/1987 | Schmitz |
| 4,744,377 | A | 5/1988 | Dolan, Jr. |
| 4,914,988 | A | 4/1990 | Chang |
| 4,922,934 | A | 5/1990 | Gatti |
| 4,988,502 | A * | 1/1991 | Ounanian et al. ............ 424/63 |
| 5,007,442 | A | 4/1991 | Hirzel |
| 5,086,793 | A | 2/1992 | Kingsford |
| 5,186,728 | A | 2/1993 | Fong |
| 5,253,382 | A * | 10/1993 | Beny .................. 15/22.1 |
| 5,383,242 | A | 1/1995 | Bigler et al. |
| 5,435,034 | A | 7/1995 | Bigler et al. |
| 5,492,136 | A | 2/1996 | Edmonds |
| 5,575,579 | A | 11/1996 | Joulia |
| 5,816,728 | A | 10/1998 | Nardolillo et al. |
| 5,822,821 | A | 10/1998 | Sham |
| 5,937,871 | A | 8/1999 | Clay |
| 6,142,692 | A | 11/2000 | Garcia |
| 6,145,514 | A | 11/2000 | Clay |
| 6,295,994 | B1 | 10/2001 | Thayer et al. |
| 6,345,626 | B1 | 2/2002 | Bouix |
| RE37,605 | E | 3/2002 | Clay |
| 6,412,496 | B1 | 7/2002 | Gueret |
| 6,450,178 | B1 | 9/2002 | Clay |
| 6,454,674 | B1 | 9/2002 | Krzesicki et al. |
| 6,565,276 | B1 | 5/2003 | Diaz |
| 6,652,888 | B2 | 11/2003 | Rhoades |
| 6,691,716 | B2 | 2/2004 | Neuner et al. |
| 6,811,340 | B2 | 11/2004 | Petit |
| 6,948,780 | B1 | 9/2005 | Litman et al. |
| 7,025,068 | B2 | 4/2006 | Dumler |
| 7,165,906 | B2 | 1/2007 | Dieudonat et al. |
| 2001/0018061 | A1 | 8/2001 | Rhoades |
| 2001/0046506 | A1 | 11/2001 | Rhoades |
| 2001/0050089 | A1 | 12/2001 | Fitjer |
| 2003/0165550 | A1 | 9/2003 | Rhoades |
| 2004/0195063 | A1 | 10/2004 | Simonis et al. |
| 2004/0234323 | A1 | 11/2004 | Albisetti et al. |
| 2004/0244809 | A1 | 12/2004 | Gueret |
| 2005/0086752 | A1 | 4/2005 | Lee |
| 2005/0142093 | A1 | 6/2005 | Skover |
| 2005/0250076 | A1 | 11/2005 | Rhoades |
| 2005/0268409 | A1 | 12/2005 | Blaustein et al. |
| 2006/0032512 | A1 | 2/2006 | Kress et al. |
| 2006/0042647 | A1 | 3/2006 | Vogel |
| 2006/0051155 | A1 | 3/2006 | Delage |
| 2006/0228157 | A1 | 10/2006 | Dieudonat et al. |
| 2006/0272666 | A1 | 12/2006 | Wyatt et al. |
| 2006/0272668 | A1 | 12/2006 | Wyatt et al. |
| 2007/0186948 | A1 | 8/2007 | Kim et al. |
| 2007/0231050 | A1 | 10/2007 | Thiebaut |
| 2007/0261868 | A1 | 11/2007 | Gross |
| 2007/0272269 | A1 | 11/2007 | Wyatt et al. |
| 2007/0289602 | A1 | 12/2007 | Simmons |
| 2008/0011316 | A1 | 1/2008 | Malvar et al. |
| 2008/0087296 | A1 | 4/2008 | Gueret |
| 2008/0196735 | A1 | 8/2008 | Wyatt et al. |
| 2008/0196736 | A1 | 8/2008 | Wyatt et al. |
| 2009/0071499 | A1 | 3/2009 | Wyatt et al. |
| 2009/0071500 | A1 | 3/2009 | Wyatt et al. |
| 2009/0154985 | A1 | 6/2009 | Wyatt et al. |

FOREIGN PATENT DOCUMENTS

| | | |
|---|---|---|
| DE | 19950665 | 5/2000 |
| DE | 19950665 C2 | 5/2000 |
| DE | 20210482 U1 | 10/2002 |
| EP | 0289726 E | 11/1988 |
| EP | 0371501 A2 | 6/1990 |
| EP | 0848920 A1 | 6/1998 |
| EP | 0 848 920 B1 | 3/2003 |
| FR | 2002-16283 | 6/2004 |
| GB | 846 639 A | 8/1960 |
| GB | 1 502 532 A | 3/1978 |
| JP | 04-040905 | 2/1992 |
| JP | 8289815 A2 | 11/1996 |
| JP | 1996289815 A | 11/1996 |
| JP | 2005095531 A | 4/2005 |
| KR | 20-0326065 | 8/2003 |
| KR | 2020030012684 | 8/2003 |
| KR | 20-0334143 | 11/2003 |
| KR | 2020030025327 | 11/2003 |
| KR | 20-0341762 | 2/2004 |
| KR | 2020030030514 | 2/2004 |
| KR | 20-0356837 | 7/2004 |
| KR | 2020040011077 | 7/2004 |
| KR | 20-0358513 | 8/2004 |
| KR | 2020040010980 | 8/2004 |
| KR | 20-0393379 | 8/2005 |
| KR | 2020050016644 | 8/2005 |
| KR | 20-0396785 | 9/2005 |
| KR | 2020050016643 | 9/2005 |
| KR | 20-0404002 | 12/2005 |
| KR | 2020050028145 | 12/2005 |
| KR | 20-0416525 | 5/2006 |
| KR | 20-0416536 | 5/2006 |
| KR | 2020060004384 | 5/2006 |
| KR | 2020060004826 | 5/2006 |
| WO | WO-00/54623 A1 | 9/2000 |
| WO | WO-2004/077987 A1 | 9/2004 |
| WO | WO-2006/090343 A1 | 8/2006 |
| WO | WO 2006/090343 A1 | 8/2006 |
| WO | WO 2006/132459 A1 | 12/2006 |
| WO | WO-2006/132459 A1 | 12/2006 |
| WO | WO 2007/060438 A2 | 5/2007 |
| WO | WO 2007/094552 A1 | 8/2007 |
| WO | WO 2008/051067 A2 | 5/2008 |

OTHER PUBLICATIONS

USPTO Office Action rejections/objections from co-pending U.S. Appl. No. 11/143,829, filed Jun. 2, 2005, Inventor: Peter Jonathan Wyatt et al., mail dates Apr. 6, 2009, Feb. 25, 2008 and Sep. 2, 2008; 23 pages.

USPTO Office Action rejections/objections from co-pending U.S. Appl. No. 11/677,326, filed Feb. 21, 2007, Inventor: Peter Jonathan Wyatt et al., mail date Aug. 14, 2009; 6 pages.

USPTO Office Action rejections/objections from co-pending U.S. Appl. No. 11/677,338, filed Feb. 21, 2007, Inventor: Peter Jonathan Wyatt et al., mail date Jun. 18, 2009; 7 pages.

USPTO Office Action rejections/objections from co-pending U.S. Appl. No. 11/6773509, filed Feb. 21, 2007; Inventor: Peter Jonathan Wyatt et al., mail date Jun. 18, 2009; 6 pages.

* cited by examiner

    
Fig. 7   Fig. 8   Fig. 9   Fig. 10   Fig. 11
 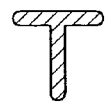  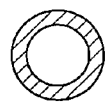 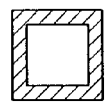
Fig. 12   Fig. 13   Fig. 14   Fig. 15   Fig. 16
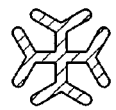   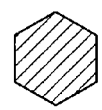
Fig. 17   Fig. 18   Fig. 19   Fig. 20
 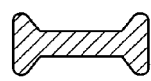 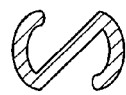
Fig. 21   Fig. 22   Fig. 23
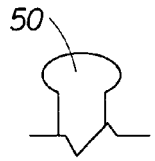 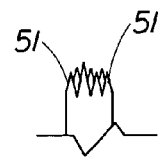  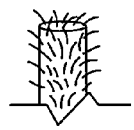
Fig. 24   Fig. 25   Fig. 26   Fig. 27
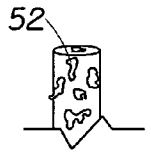
Fig. 28

74 74 72 74 74

72 72 74 74

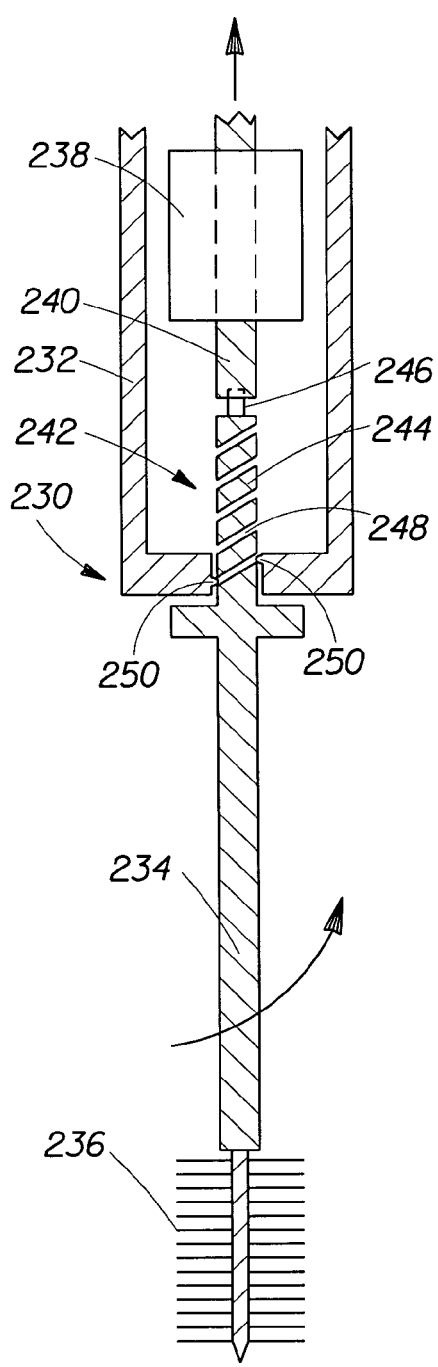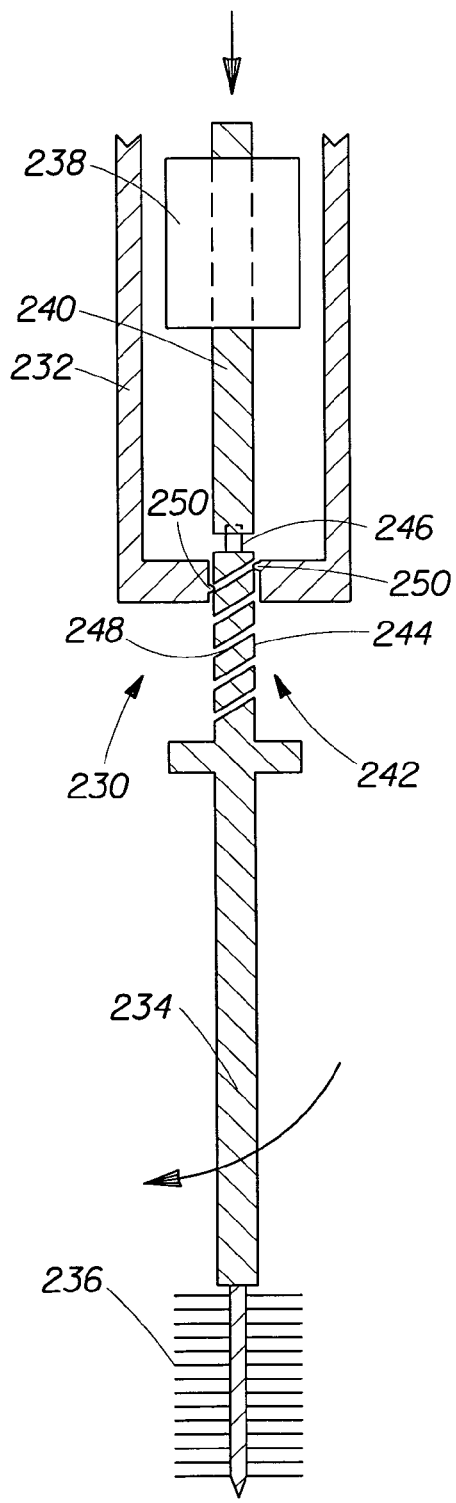
Fig. 78A
Fig. 78B

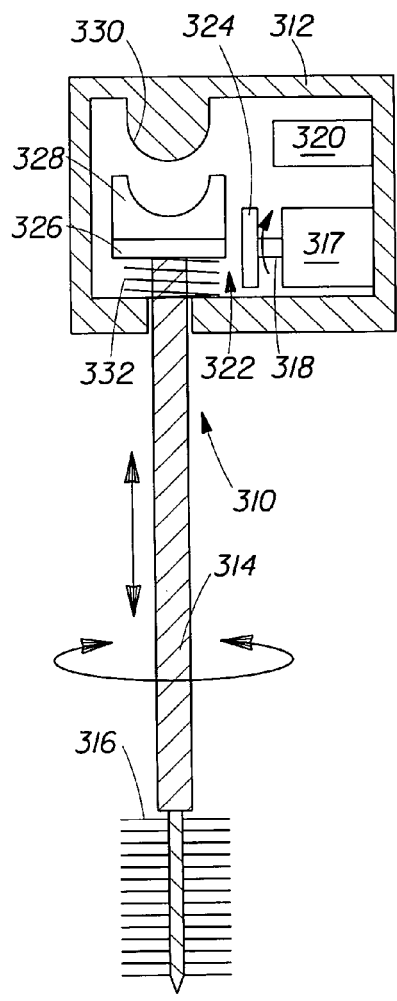
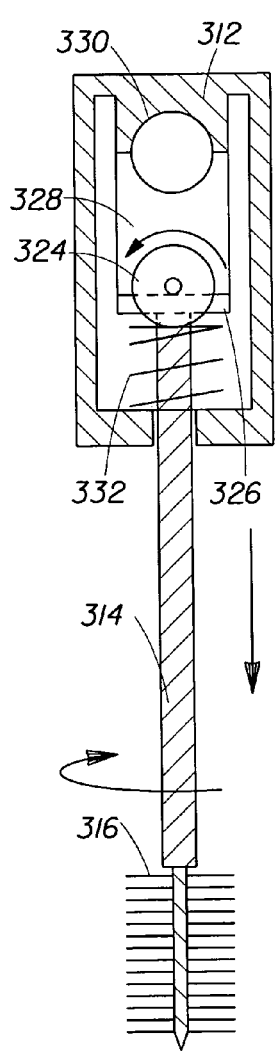
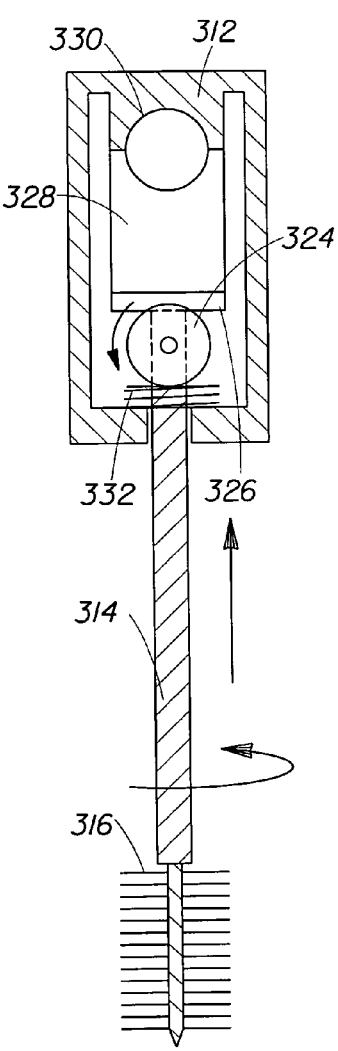
Fig. 81A
Fig. 81B     Fig. 81C

COSMETIC APPLICATOR

FIELD OF THE DISCLOSURE

The present disclosure generally relates to cosmetic applicators and, more particularly, to applicators for applying cosmetic material to keratinous fibers, such as eyelashes.

BACKGROUND OF THE DISCLOSURE

Various types of cosmetic applicators are known in the art. Brushes for applying mascara to eyelashes, for example, generally include a stem having a first end attached to a handle. An applicator head, such as brush bristles, are coupled to a second end of the stem. In use, the brush head loaded with mascara is applied to the eyelashes.

Mascaras come in a variety of forms including cakes or blocks, creams, gels, semi-solids, and low viscosity liquids. Cake mascaras were originally the most popular form consisting of at least 50% soap with the pigment mixed in with the soap cakes. With a wet brush, the mascara could be lathered and then applied to the lashes resulting in a satisfactory smooth application, but with a thin cosmetic coating on the individual lashes. The primary drawback was that the film on the lashes was very water soluble and prone to smudging and running on the skin around the perimeter of the eye. As a resolution, waxes were incorporated into mascara compositions thereby improving their water-resistant properties. Unfortunately, the smoothness of the application was adversely affected. That is, as the viscosity of the mascara formulation increased, it became increasingly harder to apply, messier, and yielded less separation of the lashes.

With the advent of mascara applicators a means for expanding formulation options for mascaras came into existence. Creams, for example, combined with a twisted metal wire brush or wand application provided a convenient use and composition that enabled the incorporation of film formers to improve the rubbing resistance and flexibility of mascara films. This also allowed a convenient implement to separate and build the lashes. Today, there are several types of mascara formulations including anhydrous, water-in-oil emulsions, oil-in-water emulsions, and water-based mascaras that contain little or no oil phase. The emulsions, previously mentioned, may also be multiple emulsions for example, but not limited to water-in-oil-in-water emulsion. Many mascaras are water-based emulsions and contain emulsified waxes and polymers usually with pigments dispersed into the water phase. The water provides curling and application properties, while the waxes and polymers create the transfer resistant end mascara film on the lash that is colored by the pigments. Anhydrous and water-in-oil mascaras are generally referred to as waterproof mascaras, as they have superior transfer resistance, especially to water. Their high content of hydrophobic materials creates a film which contains very little materials that allow water to break up the film and make it wear away. In the case of the water-in-oil mascaras, the internal droplets of water can deliver water-soluble/dispersible materials that would otherwise not be able to be incorporated into an oily phase. The water-based mascaras are typically gelled water with a polymer to create deposition and hold of the lashes. These mascaras usually do not have colorants, although colorants can be added in.

Consumers expect particular properties from their mascara products such as adhesion to the lashes, lengthening/curling of the lashes, lack of smudging or flaking, thick lashes, and good separation of clumps of lashes. Particularly, the desire is for long, luscious, full, soft, and separated lashes. Mascaras generally distribute a smooth and relatively thin (coating thickness) film over the eyelashes producing a satisfactory array of reasonably separated lashes that are darker and thicker than bare lashes, making the eyes more noticeably beautiful. It is well understood that some lash clumping will naturally occur since lashes are arranged in both rows and columns above and below one's eye. Therefore, "separated" lashes are not necessarily envisioning every lash as a single entity. Mascara that is deemed by a user to separate well will leave more clumps of lashes than mascara that is deemed not to separate lashes well. Typically, the deposition of mascara has a coating that is 5-15 microns thick. Many "volumizing" mascaras, however, are messy and clumpy and tend to clump too many lashes together in a thick, less separated look which gives the look of fewer lashes.

Conventional mascara brushes typically require manipulation of the handle or other member, and often require repeated passes of the brush across the eyelash, to completely and uniformly coat each eyelash with mascara while maintaining or promoting separation of the eyelashes from one another. To coat the entire eyelash, for example, a user may move the brush in a vertical direction to ensure that the entire eyelash is covered. In addition, a user may rotate the brush to place different portions of the brush head in contact with the eyelash, depending on the desired amount of mascara to be applied to the eyelashes. Still further, a user may also reciprocate the brush in a horizontal direction to promote separation of the eyelashes and/or to ensure better coverage of the eyelashes. Consequently, a user must provide the motive force for applying the brush to the eyelashes and must have sufficient dexterity to manipulate the brush as needed to cover the eyelashes in a satisfactory manner. In addition, mascara application with conventional brushes requires several brush passes and therefore is inefficient.

More recently, rotating mascara brushes have been proposed in which a stem of the brush is supported for rotational movement with respect to the handle. The force for rotating the stem and attached brush head may be either manual, such as for the brushes described in U.S. Pat. No. 6,145,514 to Clay and U.S. Pat. No. 5,937,871 to Clay, or may be electrically driven, such as the brush described in U.S. Pat. No. 6,565,276 to Diaz. While these rotating stem brushes eliminate the need for a user to roll the handle during application of mascara, they do not optimally coat and separate the eyelashes. Furthermore, these brushes are limited to simple, uni-directional rotation of the brush head, and therefore are not capable of performing certain, potentially more complex, application techniques.

In addition, various types of applicators have been designed which are adapted to impart different types of eyelash effects. For example, a first brush design may promote separation of eyelashes while a second brush design promotes volume or coverage of the eyelashes. Consequently, a user must use two separate brushes or, if a single brush head is provided with both types of brush designs, the user must reposition the handle to use both sides.

SUMMARY OF THE DISCLOSURE

The present disclosure relates to apparatus for applying a cosmetic. For example, the apparatus may include a handle, a stem defining a longitudinal stem axis and having a first end coupled to the handle and a second end, and an applicator head coupled to the stem second end and supported for movement relative to the handle in a direction substantially parallel to the stem axis. An actuator may be operatively coupled to the applicator head for moving the applicator head in an axial motion comprising a forward stroke and a reverse stroke. The applicator further can include a container wherein the container can contain a cosmetic such as mascara composition.

Another embodiment relates to an apparatus for applying a cosmetic having a handle, a stem defining a longitudinal stem axis and having a first end coupled to the handle and a second end, and an applicator head coupled to the stem second end and supported for movement relative to the handle in a direction substantially parallel to the stem axis. An actuator may be operatively coupled to the applicator head for moving the applicator head in a composite motion including an axial component substantially parallel to the stem axis and having a forward stroke and a reverse stroke, and a rotational oscillating component.

A further embodiment relates to an apparatus for applying a cosmetic including a handle, a stem defining a longitudinal stem axis and having a first end coupled to the handle and a second end, and an applicator head coupled to the stem second end and supported for movement relative to the handle in a direction substantially parallel to the stem axis. A motor is provided having a rotating motor shaft and a transmission coupling is disposed between the motor shaft and the applicator head for automatically converting rotation of the motor shaft in one direction into axial movement of the applicator head, the axial movement having a forward stroke and a reverse stroke.

BRIEF DESCRIPTION OF THE DRAWINGS

FIGS. 7-28 show various examples of protrusion cross-sectional shapes;

FIGS. 78A and 78B are schematic side elevation views, in cross-section, of an applicator having a transmission coupling for converting an axial actuator motion into a composite motion of an applicator head having a rotational oscillation component and an axial movement component;

FIGS. 81A-C are schematic side elevation views, in cross-section, of an applicator having a transmission coupling for converting a uni-directional motor rotation into a composite motion of an applicator head having a rotational oscillation component and an axial movement component;

While the specification concludes with claims particularly pointing out and distinctly claiming the subject matter that is regarded as the present invention, it is believed that the invention will be more fully understood from the following description taken in conjunction with the accompanying drawings. None of the drawings are necessarily to scale.

DETAILED DESCRIPTION

A cosmetic applicator having an applicator head adapted for use on a rotating stem is disclosed herein. The applicator head includes protrusions that are spaced sufficiently to allow keratinous fibers such as eyelashes to penetrate therebetween. In accordance with other embodiments, a cosmetic applicator capable of complex movements such as variable speed rotation, oscillating rotation, oscillating movement along a stem axis, and vibrational movement of the applicator head are disclosed herein for improving coverage and separation of the keratinous fibers. The applicator is particularly suited for applying mascara (which may be any one of the materials noted above, or combinations thereof) to eyelashes.

Figure 1:
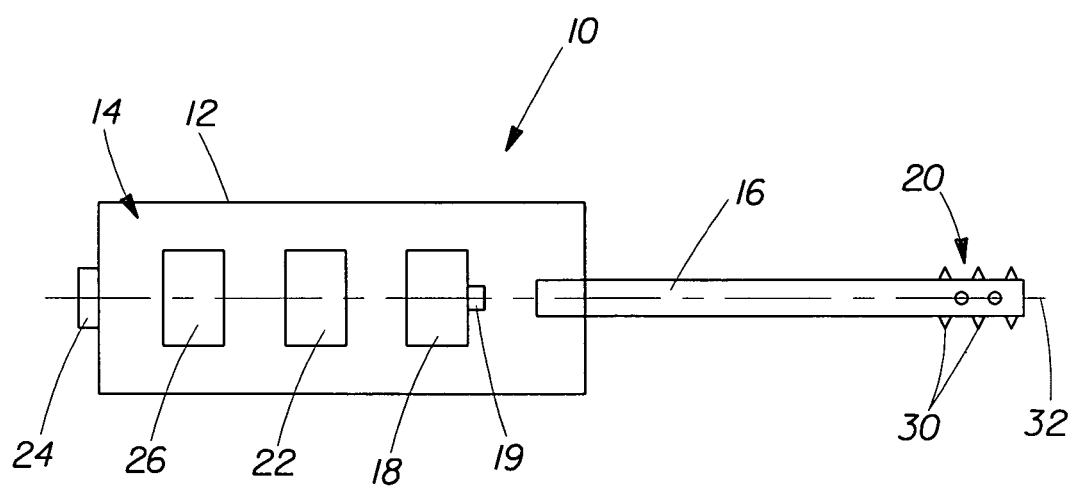
FIG. 1 is a partially schematic side elevation view, in cross-section, of one embodiment of a cosmetic applicator.

As illustrated in partial schematic form in FIG. 1, an applicator 10 includes a handle 12 defining a housing 14. A stem 16 is supported for rotation with respect to the handle 12 by conventional means. A motor 18 includes a motor shaft 19 coupled to a first end of the stem 16. A second end of the stem 16 defines an applicator head 20. A battery 22 is operatively coupled to the motor 18 and a switch 24 may be manually actuated to selectively deliver battery power to the motor 18. The applicator 10 may further include a controller 26 coupled between the battery 22 and the motor 18 for controlling operation of the motor 18.

In operation, a user may actuate the switch 24 to selectively deliver potential energy from the battery 22 to the motor 18. In response, the motor may rotate the motor shaft and stem 16 attached thereto. As a result, the applicator head also rotates. While the embodiment illustrated in FIG. 1 includes a battery for providing potential energy to the motor 18, it will be appreciated that other types of energy sources may be used such as mechanical potential energy stored in a resilient member such as a spring or rubber band.

The applicator head 20 includes one or more elements projecting from the stem for separating and applying cosmetic to keratinous fibers, such as eyelashes. While the applicator element may be provided as a conventional twisted wire brush, we have found it preferable to use molded protrusions. As used herein, a "protrusion" is a member that extends generally away from or into a base surface of the applicator head. As such, a "protrusion" provides a localized area that is not continuous with the surrounding base surface. While protrusions typically extend outwardly away from the base surface, they may also be inverted to project inwardly to form a recess.

In the illustrated embodiment, the molded protrusions are formed as elongate fingers 30 having a base end coupled to the stem 16 and an opposite free end. In the illustrated embodiment, the cross-sectional area of each finger 30 gradually narrows from the base end to the free end, and each finger is oriented to extend substantially perpendicular with respect to an axis 32 of the stem 16. It will be appreciated that the fingers may diverge from the base so that the tip is larger, or the fingers may not taper at all but instead have substantially consistent dimensions. Furthermore, the fingers may extend at oblique angles with respect to the stem axis 32.

The fingers 30 are spaced along the stem 16 and have a free end sized such that each finger 30 may penetrate between adjacent keratinous fibers. The spacing allows the fingers 30 to be inserted between fibers even as the applicator head 20 is rotated, thereby maximizing the fiber surface area engaged by each finger 30 and promoting separation of adjacent fibers. The protrusions should be spaced far enough to allow eyelashes to penetrate between adjacent protrusions yet close enough to separate adjacent eyelashes. Accordingly, the gap between adjacent protrusions may be approximately 0.2 to 3.0 mm.

Figure 2:
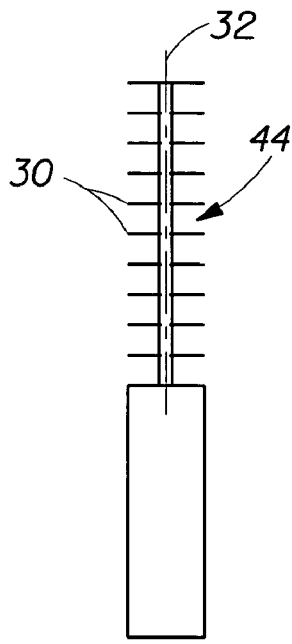
FIGS. 2-6 are partially schematic side elevation views of alternative protrusion arrangements for use with the cosmetic applicator of FIG. 1.

While each of the protrusions illustrated in FIG. 1 extends from a localized area of the stem 16 circumference, other areas of engagement between the stem and the protrusions may be used. As illustrated in FIG. 2, for example, each protrusion 30 may be substantially disc-shaped and have a base end with a substantially annular shape. In the illustrated embodiment, the base end preferably engages no more than one complete circumference of the stem 16 surface to minimize snagging of the eyelashes as the protrusions 30 rotate. Other disc shapes traversing more than one complete circumference of the stem may also be used. For example, an elongate stem having a rectangular cross-section may be twisted so that the corners of the stem form localized extensions while the faces of each side of the stem form recesses or gaps between adjacent corners. Protrusions are attached to the surface of the stem to define an irregular or non-uniform applicator head profile generally matching the shape of the stem. The protrusions may have a length that is 10% to 400% of the length of the stem extensions.

Figure 3:
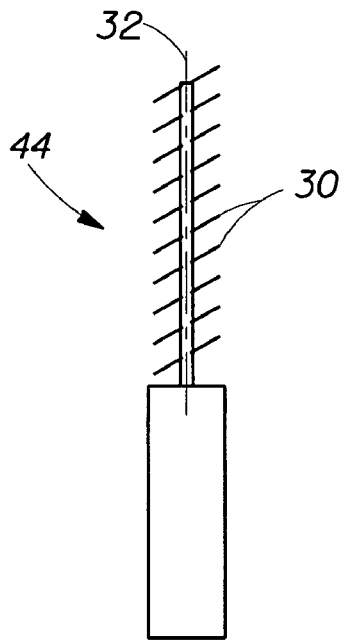
Figure 4:
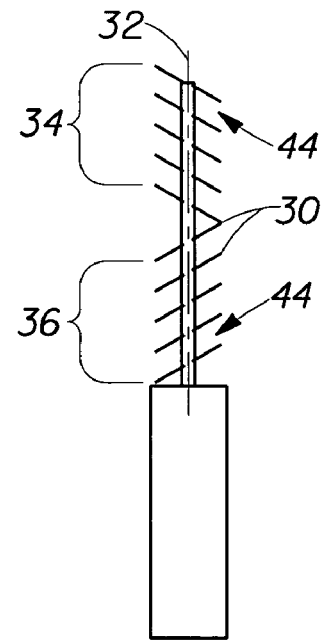
Figure 5:
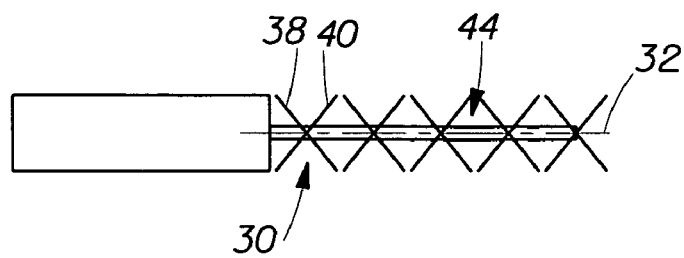
Figure 6:
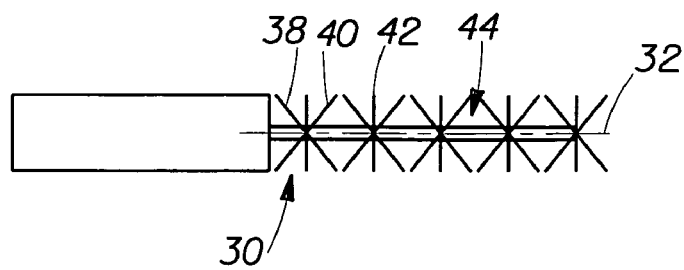

While the disc-shaped protrusion 30 is illustrated in FIG. 2 as a single molded member, it will be appreciate that the protrusion 30 may be formed of a plurality of members such as bristles that are arranged in the disc-shaped pattern. The protrusions 30 may extend substantially perpendicular to the stem axis 32 to form straight rows of protrusions. Alternatively, all or some of the protrusions 30 may be oriented at a same oblique angle with respect to the stem axis 32 to form diagonal rows as illustrated in FIG. 3, or may include a first set of protrusions 34 oriented at a first oblique angle and a second set of protrusions 36 oriented at a second oblique angle different from the first angle to form reverse diagonal rows, as illustrated in FIG. 4. Each protrusion 30 may include a first protrusion segment 38 extending at a first oblique angle and a second protrusion segment 40 extending at a second oblique angle so that the first protrusion segment intersects the second protrusion segment 40 to form cross-diagonal rows, as illustrated in FIG. 5. In addition to the first and second protrusion segments 38, 40, each protrusion 30 may include a third protrusion segment 42 extending substantially perpendicular to the stem axis 32 to form combination rows, as illustrated in FIG. 6. In each of the forgoing embodiments, a circumferential gap 44 is provided between adjacent protrusions 30 to allow insertion of the protrusions between adjacent keratinous fibers. Each gap is preferably approximately 0.2 to 3.0 mm to provide sufficient space for an eyelash to penetrate between adjacent protrusions while providing at least some level of eyelash separation.

The cross-sectional shape of the protrusions 30 may be varied without departing from the scope of this disclosure. As illustrated in FIG. 1, the protrusions are provided as fingers having substantially circular cross-sectional shapes. The protrusions may have various types of cross-sectional shapes in additional to circular, such as any one of the shapes shown diagrammatically in FIGS. 7 to 23, for example a circular shape with a flat as shown in FIG. 7, a flat shape as shown in FIG. 8, a star shape, e.g. in the form of a cross as shown in FIG. 9, or having three branches as shown in FIG. 10, a U-shape as shown in FIG. 11, an H-shape as shown in FIG. 12, a T-shape as shown in FIG. 13, a V-shape as shown in FIG. 14, a hollow shape, e.g. a circular shape as shown in FIG. 15, or a polygonal shape in particular a square shape as shown in FIG. 16, a shape that presents ramifications, e.g. a snowflake shape as shown in FIG. 17, a polygonal shape, e.g. a triangular shape as shown in FIG. 18, a square shape as shown in FIG. 19, or a hexagonal shape as shown in FIG. 20, an oblong shape, in particular a lens shape as shown in FIG. 21, or an hourglass shape as shown in FIG. 22. It is also possible to use protrusions having portions which are hinged relative to one another as shown in FIG. 23.

The ends of the protrusions may be formed with various shapes or include various structures. Where appropriate, the protrusions may be subjected to treatment for forming respective end balls 50 as shown in FIG. 24, end forks 51 as shown in FIG. 25, or tapering tips as shown in FIG. 26. The protrusions may also be flocked as shown in FIG. 27 or made by extruding a plastic material containing a filler of particles 52 so as to impart micro-relief to the surface of the bristles as shown in FIG. 28 or so as to confer magnetic or other properties thereon.

The protrusions may have an exterior surface particularly adapted to transfer cosmetic material from a base of the protrusion to a free end. For example, each protrusion may include an exterior coating having a low surface energy to more readily transfer product to the lashes. The coating may be particularly suited for use with cosmetic material, such as the mascara materials noted above in the background.

Figure 29:
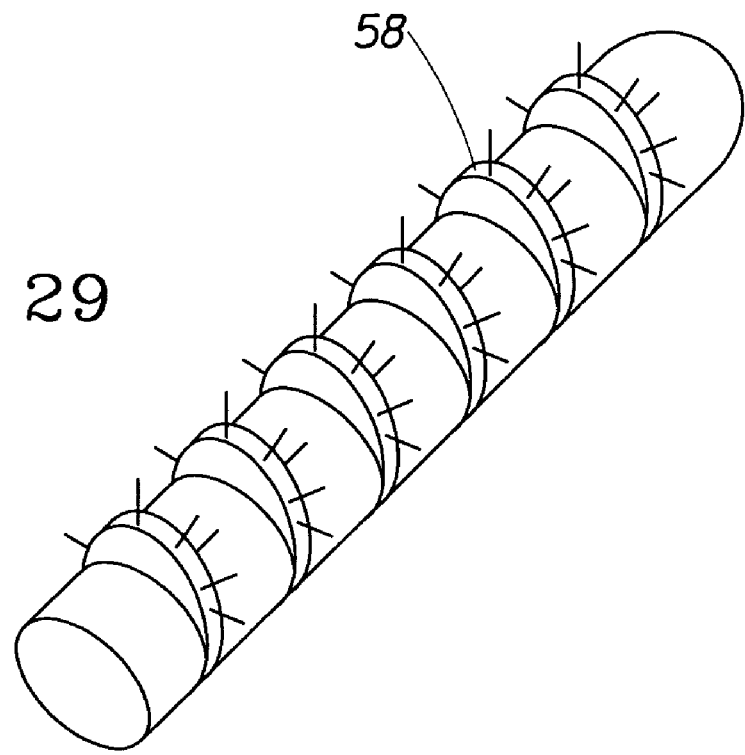
FIGS. 29 and 30 are perspective views of applicator heads having alternative protrusions.
Figure 30:
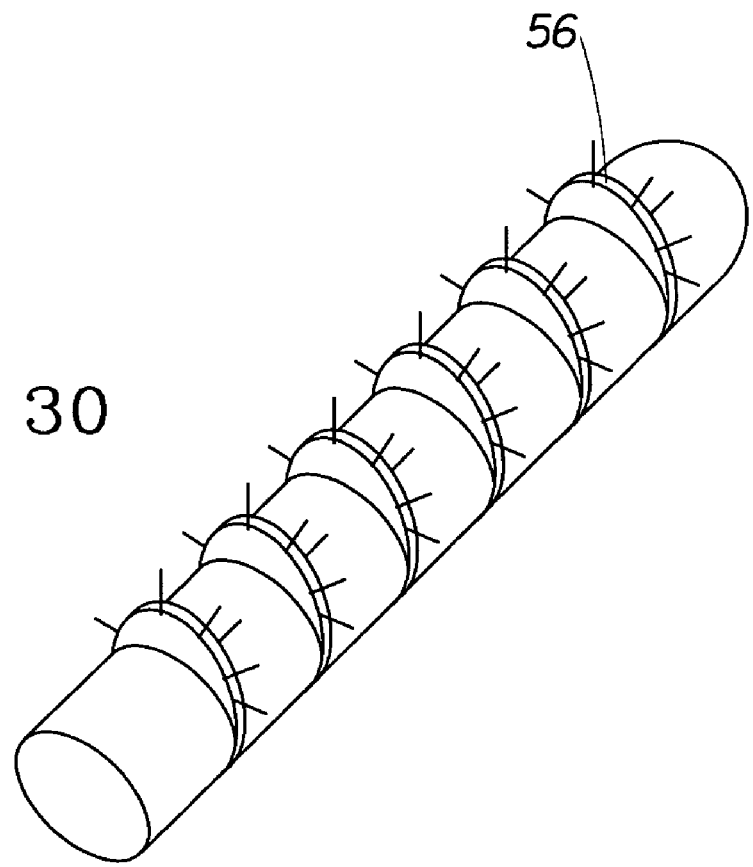

In addition to the elongate profile illustrated in FIG. 1, at least some of the protrusions may be somewhat shorter, such as protruding discs 56, dimples, or ridges 58 extending from an exterior surface of the stem 16, as illustrated in FIGS. 29 and 30. Still further, protrusions having a broad range of flexibility or stiffness may be used.

Figure 31A:
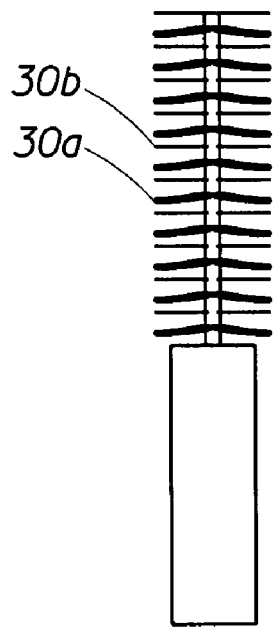
FIGS. 31A-C illustrate an applicator head having a combination of flexible and stiff protrusions.
Figure 31B:
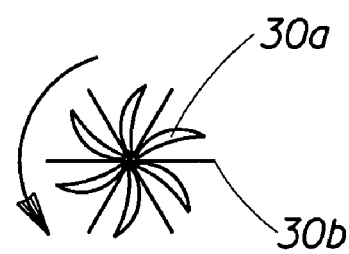
Figure 31C:
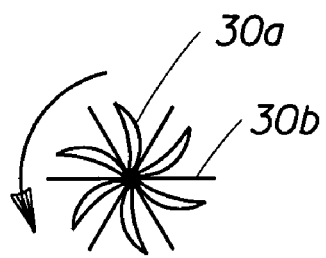

The applicator head 20 may include a variety of protrusions having different shapes or displaying different properties. For example, the applicator head 20 may include a first set of protrusions having a first cross-sectional shape and a second set of protrusions having a second cross-sectional shape. Also, the first set of protrusions 30a may have a first stiffness while the second set of protrusions 30b has a second, different stiffness. By using protrusions of varying stiffness, rotation of the applicator head will cause the more flexible protrusions to deflect to a greater degree than the stiffer protrusions, as illustrated in FIGS. 31A-C.

Figure 32:
FIGS. 32-42 are diagrammatic cross-sections showing possible cross-sectional shapes for the stem.
Figure 33:
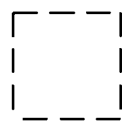
Figure 34:
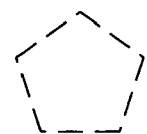
Figure 35:
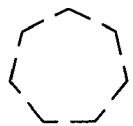
Figure 36:
Figure 37:
Figure 38:
Figure 39:
Figure 40:
Figure 41:
Figure 42:
Figure 43:
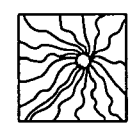
FIG. 43 shows how the center of the stem may be off-center.

The stem 16 may have a uniform, circular cross-section or a non-circular shape such as the polygonal, e.g. triangular section shown in FIG. 32. As further examples, the stem 16 may have a square cross-sectional shape as shown in FIG. 33, a pentagonal shape as shown in FIG. 34, a hexagonal shape as shown in FIG. 35, or an oval shape as shown in FIG. 36. The stem 16 may have at least one notch area 60, which may be outwardly concave as shown in FIGS. 37 and 38, wherein the notch presents a cross-section that is constant or otherwise. The notch 60 may be made in a circular cross-sectional shape as shown in FIG. 37, or a non-circular cross sectional shape, e.g., triangular section, as shown in FIG. 38. In the triangular case, the notch 60 may constitute an entire side of the triangle as shown, in which case the applicator presents a facet that is concave. The stem 16 shape may include a plane facet 61, as illustrated in FIG. 39. The profile may alternatively include at least one indentation 62, such as the three indentations shown in FIG. 40. A stem 16 shape having two indentations 62 is shown in FIG. 41, while a stem shape with one indentation 62 is shown in FIG. 42. The applicator head 20 may define a cross-sectional profile that is constant or otherwise, and its core may be rectilinear or otherwise. The stem 16 may be centered or off-center relative to the outline of the cross-sectional profile, as shown in FIG. 43.

Figure 44:
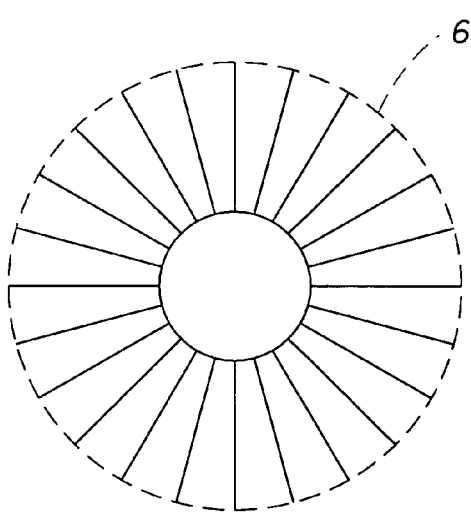
FIGS. 44-56 are plan views of applicator heads having various distributions of protrusions about a circumference.
Figure 49:
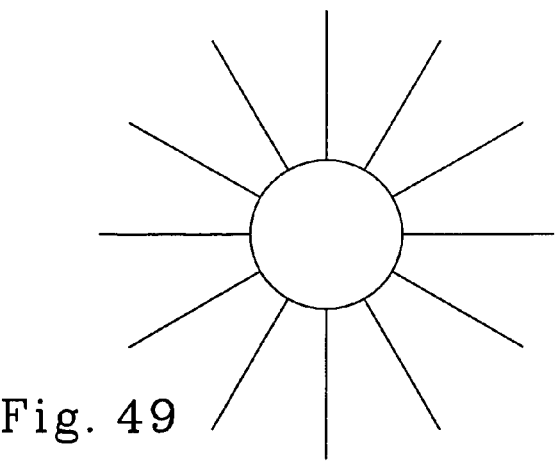
Figure 54:
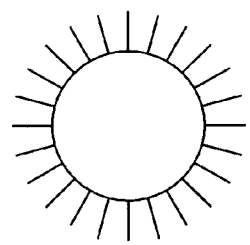
Figure 55:
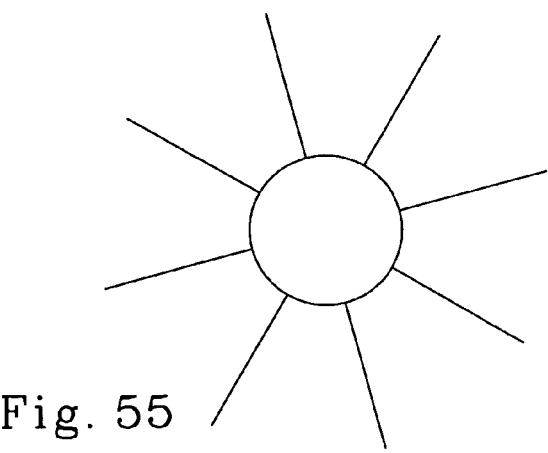

The stem 16 may be circular and have protrusions of uniform length to define a circular applicator head profile 64, as shown in FIG. 44. The protrusions may be closely spaced as shown in FIG. 44, intermediately spaced as shown in FIG. 49, or remotely spaced as shown in FIG. 55. Additionally, each protrusion may have a relatively longer length as shown in FIG. 44 or a relatively shorter length as shown in FIG. 54.

Figure 45:
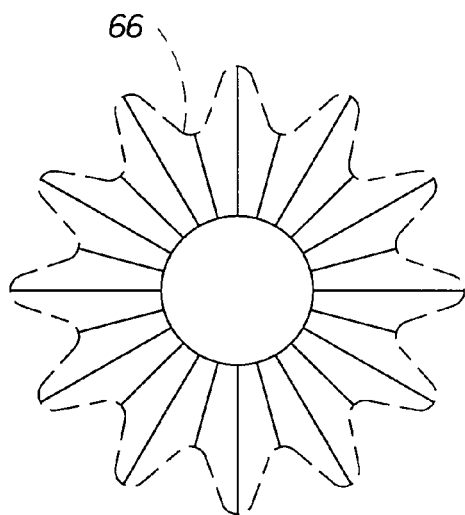
Figure 46:
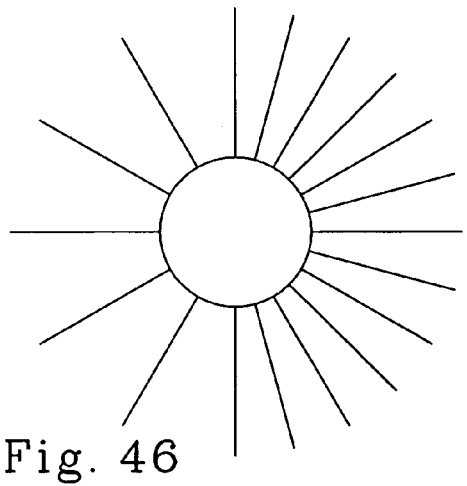
Figure 47:
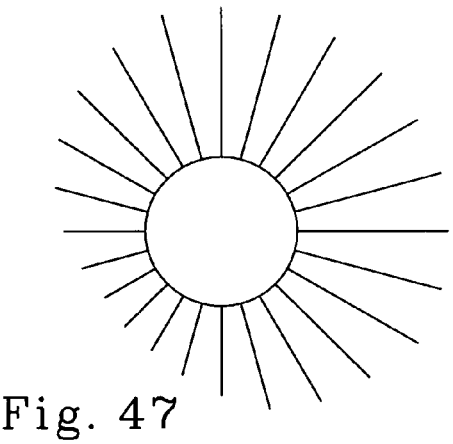
Figure 48:
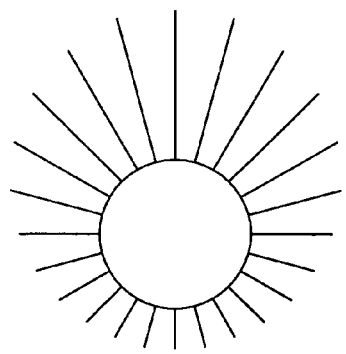
Figure 50:
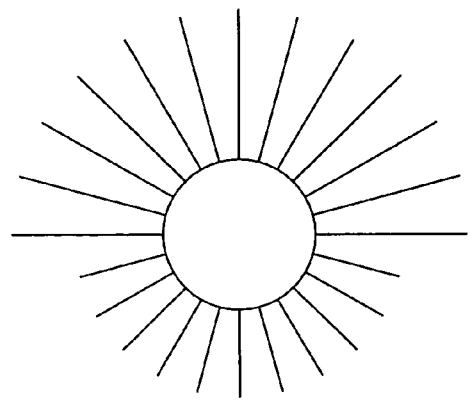
Figure 51:
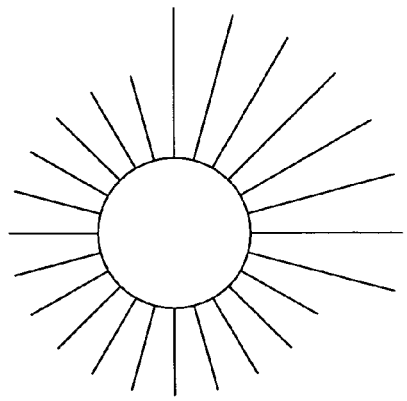
Figure 52:
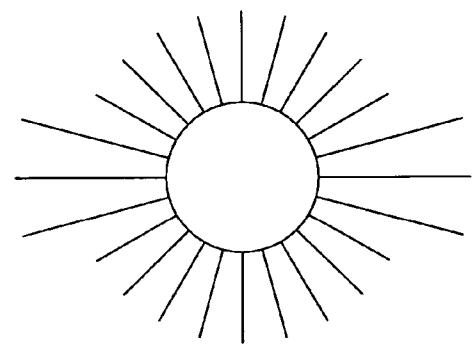
Figure 53:
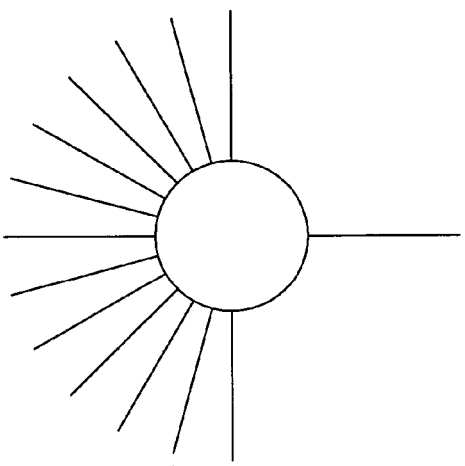
Figure 56:
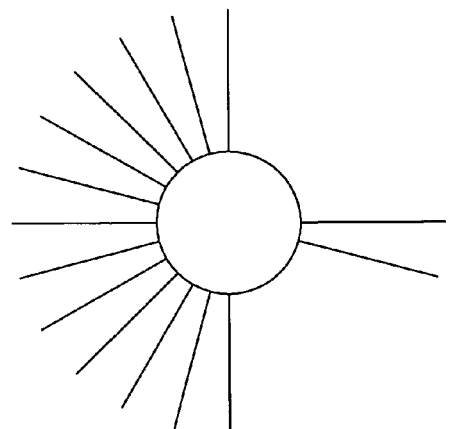
Figure 57A:
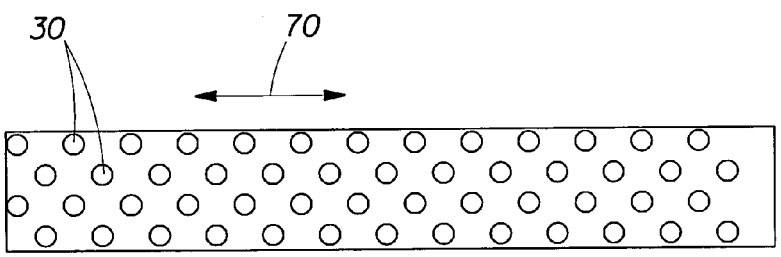
FIGS. 57-63 are plan views of each quadrant of various applicator heads showing distributions of protrusions along an axial length of the applicator head.
Figure 57B:
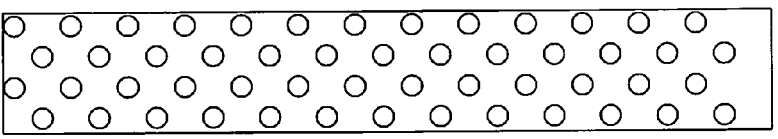
Figure 57C:
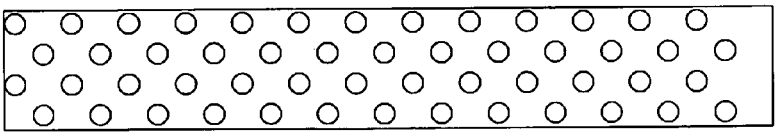
Figure 57D:
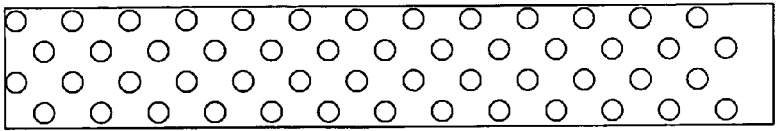
Figure 58A:
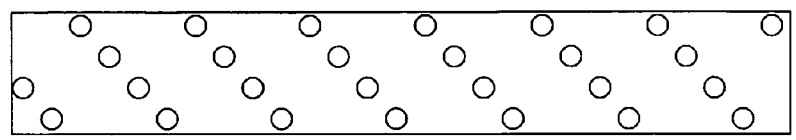
Figure 58B:
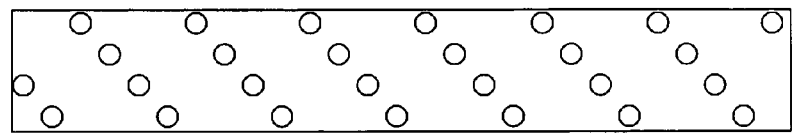
Figure 58C:
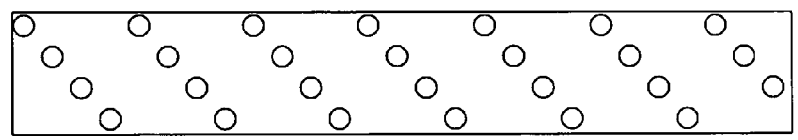
Figure 58D:
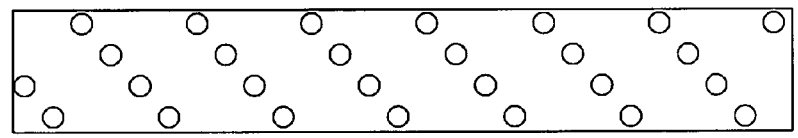
Figure 59A:
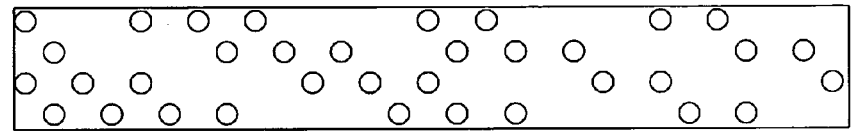
Figure 59B:
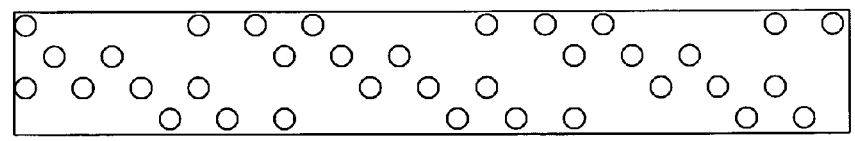
Figure 59C:
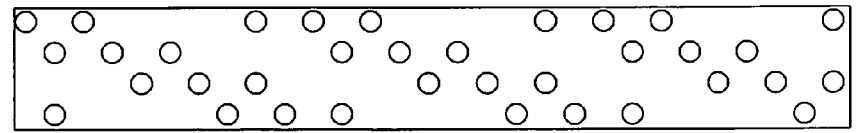
Figure 59D:
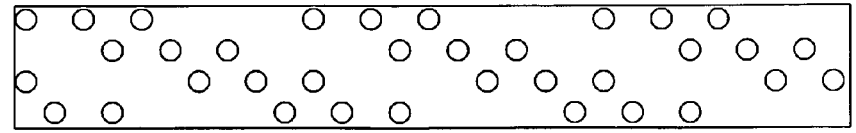
Figure 60A:
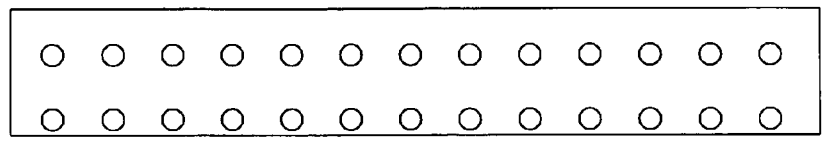
Figure 60B:
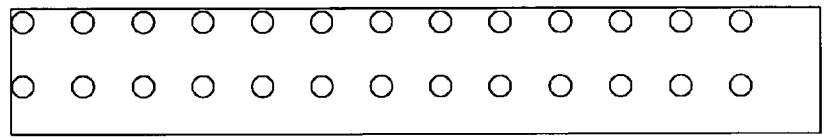
Figure 60C:
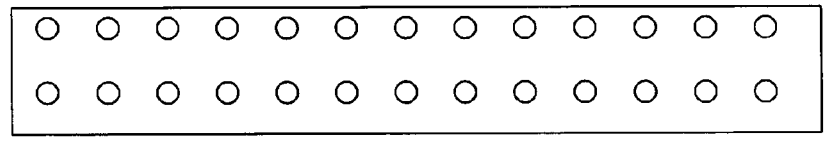
Figure 60D:
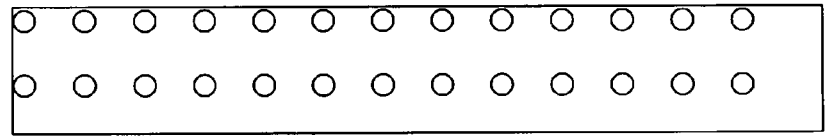
Figure 61A:
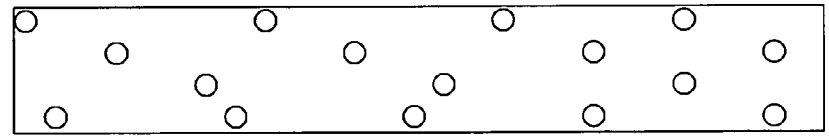
Figure 61B:
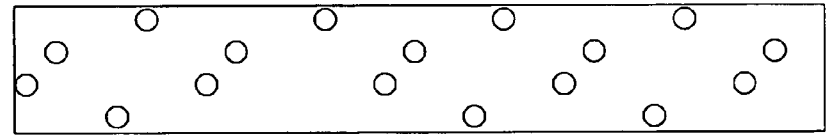
Figure 61C:
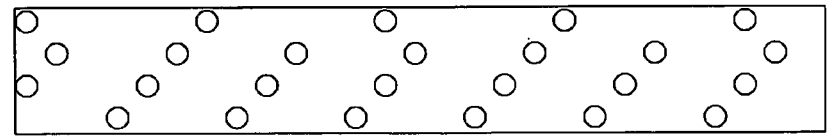
Figure 61D:
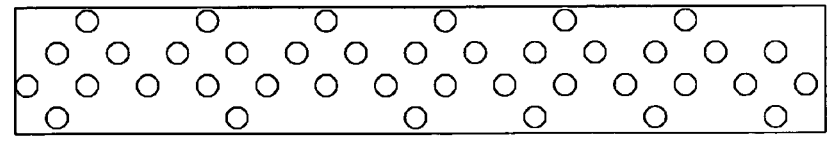
Figure 62A:
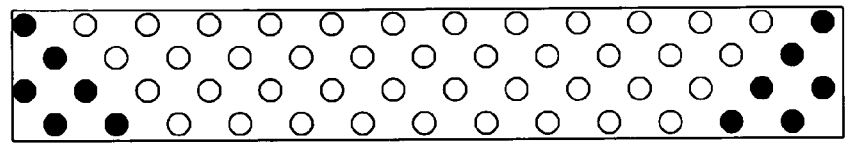
Figure 62B:
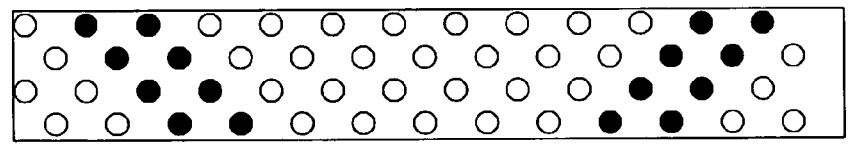
Figure 62C:
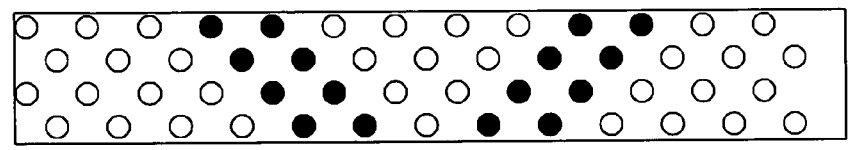
Figure 62D:
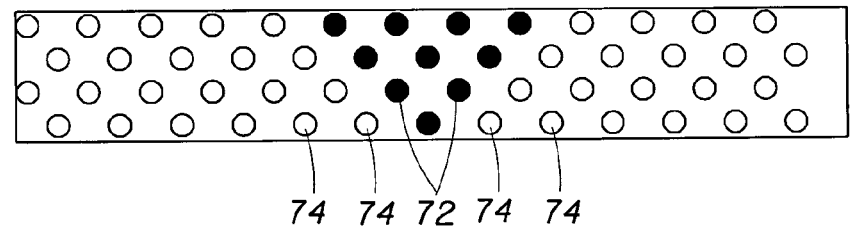
Figure 63A:
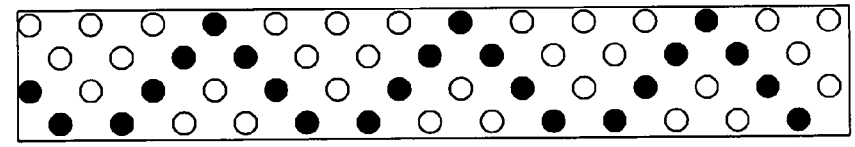
Figure 63B:
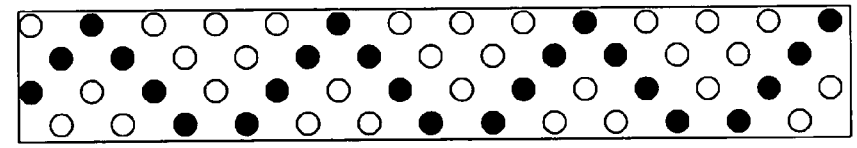
Figure 63C:
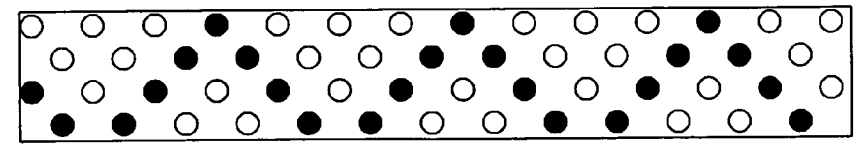
Figure 63D:
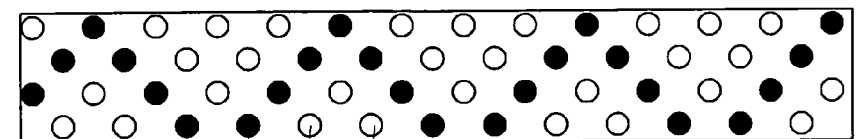

Alternatively, the shape of the stem 16 and/or the length and spacing of the protrusions may be varied to define a non-circular applicator head profile. For example, the length of the protrusions may alternate between short and long lengths around the circumference of the stem 16 to define a cross-sectional applicator head profile 66 having recesses, as shown in FIG. 45. One half of the applicator may include more closely spaced protrusions while the other half of the applicator may have farther spaced protrusions to provide an applicator head having sections of varying density, as illustrated in FIG. 46. The applicator head may include protrusions of several different lengths to define an irregular applicator head profile as shown in FIGS. 47 and 48. Other possible embodiments include one half of the applicator having shorter protrusions while the other half of the applicator head 20 having longer protrusions, as shown in FIG. 50; one quadrant of the applicator head 20 having longer protrusions while the remaining three quadrants of the applicator head have shorter protrusions as shown in FIG. 51; opposing sections of longer and shorter protrusions as shown in FIG. 52; one half of the applicator head 20 having densely spaced protrusions while the other half includes a single protrusion as shown in FIG. 53; and one half of the applicator including a plurality of densely spaced protrusions while the other half includes a pair of protrusions as shown in FIG. 56.

In addition to varying the circumferential spacing of the protrusions, the axial spacing of the protrusions along the applicator head 20 may also be varied. FIGS. 57A-D illustrate four quadrants of an applicator head 20 having protrusions 30 that are substantially uniformly spaced in the axial direction, indicated by arrow 70. The pattern of protrusions is uniform to create alternating or staggered rows of protrusions lying in a plane extending substantially perpendicular to the stem axis 32. FIGS. 58A-D illustrate four quadrants of an applicator head 20 having uniformly spaced protrusions lying in a plane extending at an oblique angle with respect to the stem axis 32. FIGS. 59A-D illustrate four quadrants of an applicator head 20 having non-uniformly spaced protrusions forming a repeating pattern having areas of closer spaced protrusions and areas of farther spaced protrusions. FIGS. 60A-D illustrate four quadrants of an applicator head 20 having uniformly spaced protrusions forming aligned rows of protrusions lying in a plane extending substantially perpendicular to the stem axis 32. FIGS. 61A-D illustrate four quadrants of an applicator head in which each quadrant has a different pattern of protrusions.

The applicator head 20 may include patterns of protrusions having different lengths. As shown in FIGS. 62A-D, four quadrants of an applicator head are shown having uniformly spaced protrusions. The pattern includes shorter protrusions 72 (illustrated in a lighter tone) and longer protrusions 74 (illustrated in a darker tone). The shorter protrusions may be upright to project outwardly from the stem surface, or may be inverted to extend into the stem, and therefore may be 0-400% shorter than the longer protrusions. The shorter protrusions 72 form a V-shaped pattern extending through a rectangular field of longer protrusions 74. FIGS. 63A-D illustrate four quadrants of an applicator head in which the shorter protrusions 72 form a grid pattern while the longer protrusions 74 form a repeating square pattern inside each grid.

The applicator may include visible indicia to identify portions of the applicator having different characteristics. An asymmetrical applicator head, for example, may include a first area having protrusions with a first characteristic and a second area having protrusions with a second characteristic. The applicator head may have a first visible indicia, such as color, texture, text, or other visually discernable quality, to identify the first area and a second visible indicia to identify the second area. The different visible indicia communicate to a user that the different areas have protrusions with different characteristics, such as relative flexibilities, lengths, or motions. The visible indicia may be provided as different colors in the first and second areas. For example, the protrusion tip, entire protrusion body, or applicator head surface including protrusions associated with the first area may have a first color, while similar structure in the second area has a second color. Similarly, the first area may have a first color scheme, such as an applicator head surface with a first color and protrusions or portions thereof with a second color, while the second area has a second color scheme, such as an applicator head surface with a third color and protrusions or portions thereof with a fourth color.

As noted above, the motor 18 is coupled to the stem 16 to rotate the applicator head 20. The motor 18 preferably rotates the applicator head at a rotational speed suitable for applying mascara to keratinous fibers. Accordingly, it has been found that a speed of approximately 1 to 200 rpm may be used, with the range of approximately 5 to 100 rpm being preferable and the range of approximately 10 to 60 rpm being most preferable for certain applications. The motor speed may be fixed or may be adjustable within the appropriate range.

Figure 64:
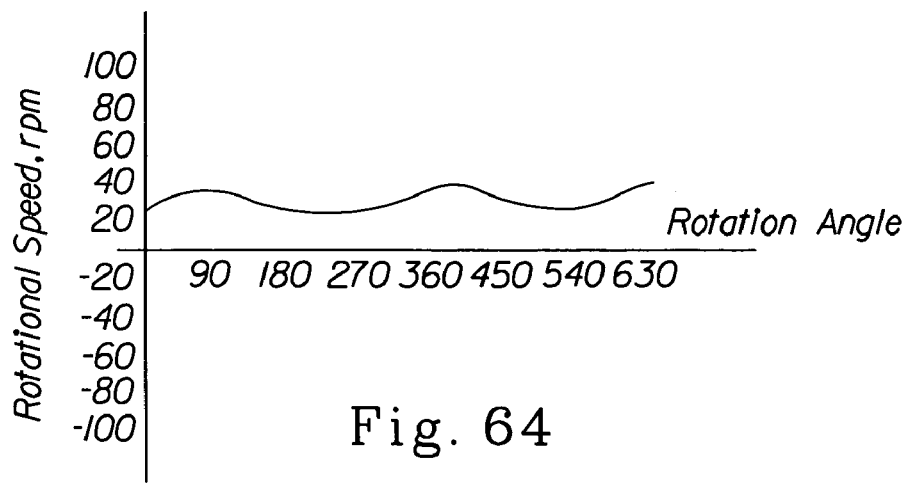
FIGS. 64 and 65 are graphs illustrating a varying rotational speed of the stem.
Figure 65:
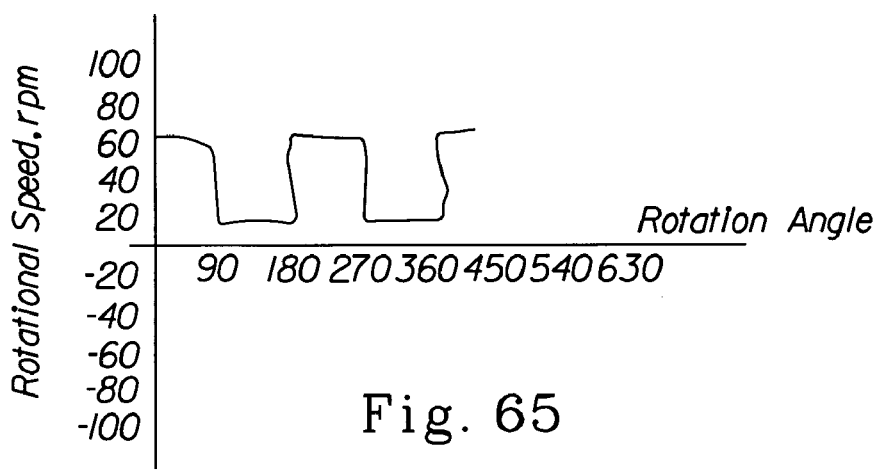
Figure 66:
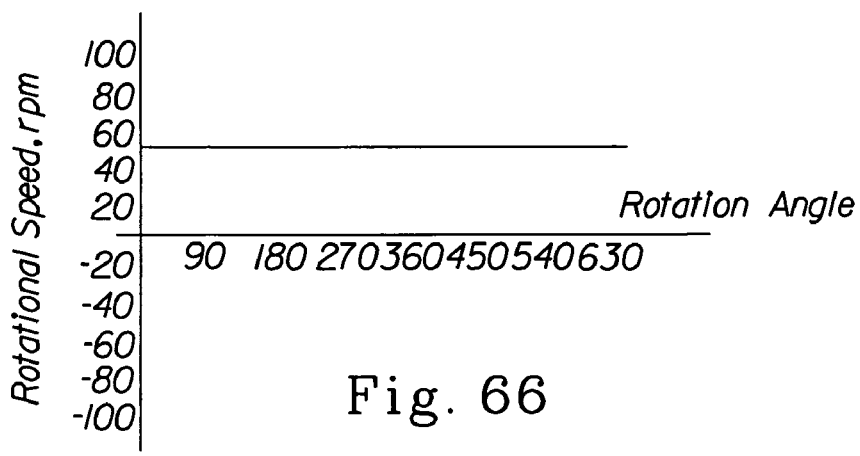
FIG. 66 is a graph illustrating a constant rotational speed of the stem.

The optional controller 26 may be provided for producing more complex movements of the applicator head. For example, the controller 26 may provide a dynamic speed signal to the motor to automatically adjust the rotational speed of the applicator head. The dynamic signal may generate a generally repeating speed pattern, such as a varying speed according to the degrees of shaft rotation, as illustrated by the graphs shown in FIGS. 64 and 65. In FIG. 64, the graph illustrates a gradually, generally sinusoidal speed fluctuation according to shaft rotation. In contrast, the graph in FIG. 65 illustrates an abrupt, step change in speed according to shaft rotation. A fixed speed is illustrated in the graph shown in FIG. 66.

The motor may be reversible to facilitate use on eyelashes associated with both the left and right eyes. It is often desirable to apply mascara using an applicator movement that begins at a base of the eyelash and progresses toward a free end. Users often hold the applicator 20 in a hand associated with the same side as the eye (i.e., the right hand to apply mascara to the right eye and the left hand to apply mascara to the left eye). Because the orientation of the applicator changes as the applicator is transferred between hands, a reversible motor advantageously allows the user to operate the applicator in the desired direction for both eyes.

When providing a reversible motor to rotate the applicator head in either direction, it is advantageous to control how a user operates the motor so that the applicator head spins in the anticipated and desired direction. While a simple toggle switch with appropriate labels may be sufficient, it may be more desirable to limit the user's ability to operate the applicator only in the desired direction.

Figure 91:
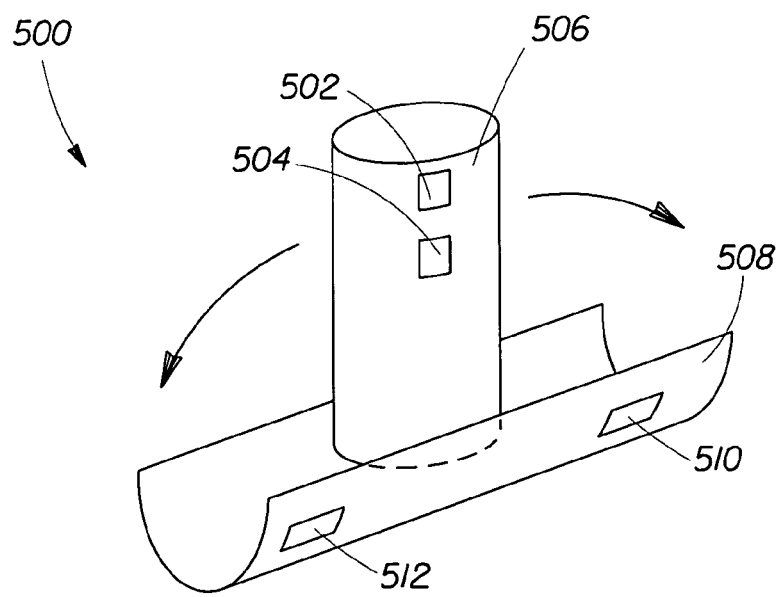
FIG. 91 is a schematic perspective view of an applicator having a shield for selectively covering a switch.

As shown in FIG. 91, for example, an applicator 500 may include two switches 502, 504, one for each direction of motor rotation. A handle 506 of the applicator 500 may include words, icons, or other indicia indicating the eye associated with each switch 502, 504. A pivoting shield 508 is coupled to the handle 506 and includes two windows 510, 512 sized to allow access to an associated switch 502, 504. The windows 510, 512 are positioned such that only the switch associated with that window is accessible when the shield is rotated in the appropriate direction. As a result, a user is prevented from operating one of the switches.

Figure 92:
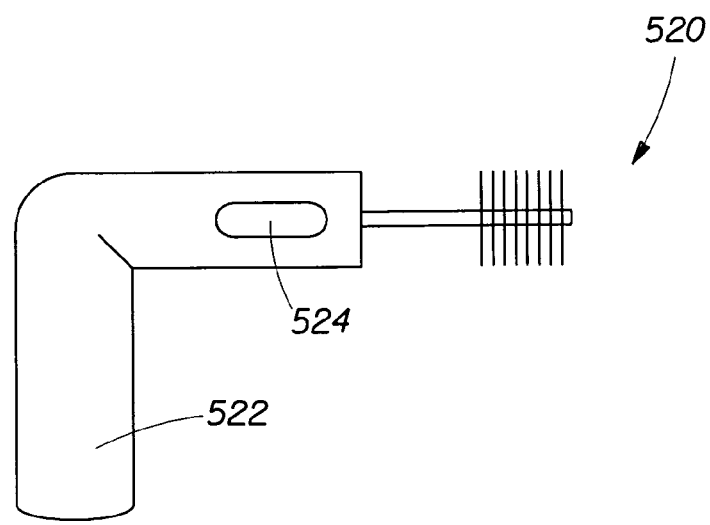
FIG. 92 is a schematic side elevation view of an applicator having two switches positioned in convenient locations for either left or right eye application.

In the alternative embodiment illustrated at FIG. 92, the applicator may position two switches such that only the appropriate switch is readily accessible when held in a certain way. An applicator 520 includes a handle 522 with two switches 524. Only one switch 524 is visible in FIG. 92, as the other switch is located on a side of the handle 522 opposite that shown in FIG. 92. The switches 524 are positioned at natural contact points of the user's hands, such as the thumbs. When the actuator is grasped in the right hand, for example, only the switch 524 for operating the applicator 520 with a motion direction appropriate for application to a right eye is easily accessible to a user. The other switch may be covered by the user's palm or may otherwise require repositioning or additional manipulation by the user to access and operate the switch. When switched to the left hand, the other switch 524 is positioned for convenient engagement by the user. Accordingly, the user is more likely to use the more accessible and convenient switch, thereby minimizing inadvertent or unexpected operation of the applicator in an undesired direction.

Still further, the applicator may be adapted to operate only in the desired direction when oriented in a certain position, such as when held to apply cosmetic to either the left or right eye. For example, the applicator may have a motor controlled by a mercury switch which reverses the polarity of the motor according to its position and the contacts it makes with the motor. The applicator handle may be shaped such that the mercury switch causes motor rotation in a first direction when held in position near the left eye and in a second, opposite direction when held in position near the right eye.

The motor 18 may also be controlled to execute a fixed degree of rotation each time the switch 24 is actuated. For example, the motor 18 may execute a quick rotation of the applicator head 20 through a predetermined angle of rotation to present a different side of the applicator head 20 toward the user. The predetermined angle of rotation may generally be approximately 0 to 270 degrees, with approximately 120 to 240 degrees being preferred and approximately 180 degrees being most preferred. This is of particular benefit where the applicator head includes sections of varying protrusion patterns, such as an applicator head having a first section with protrusions arranged to promote separation of lashes and a second section with protrusions arranged to provide volume. The quick, fixed rotation of the applicator head 20 allows a user to switch between the separator and volume sections of the applicator head simply by actuating the switch 24, without manipulating or repositioning the applicator in the hand.

Figure 67:
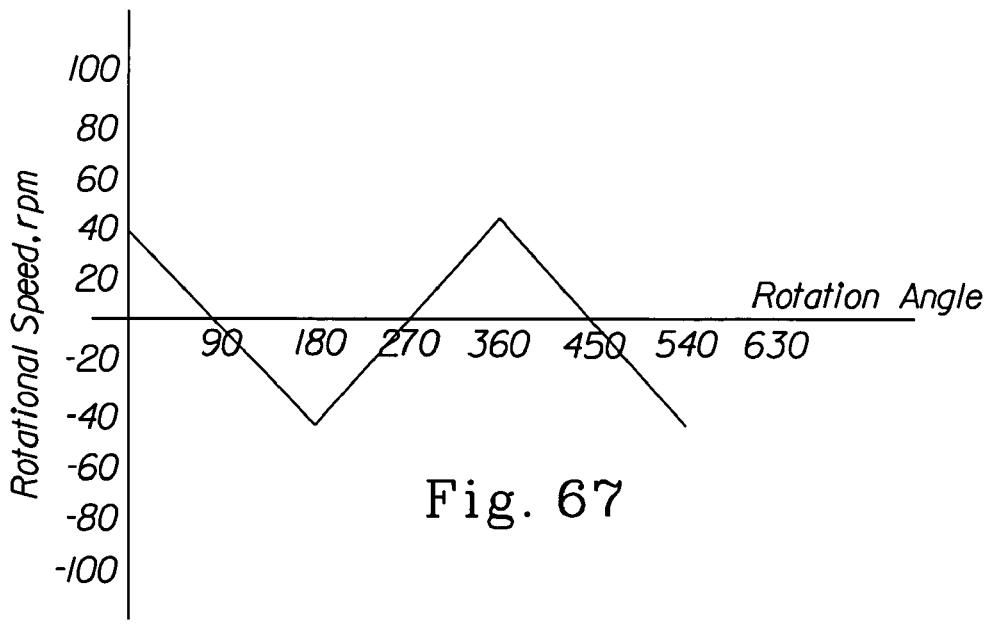
FIGS. 67 and 68 are graphs illustrating a reversible rotational speed of the stem.
Figure 68:
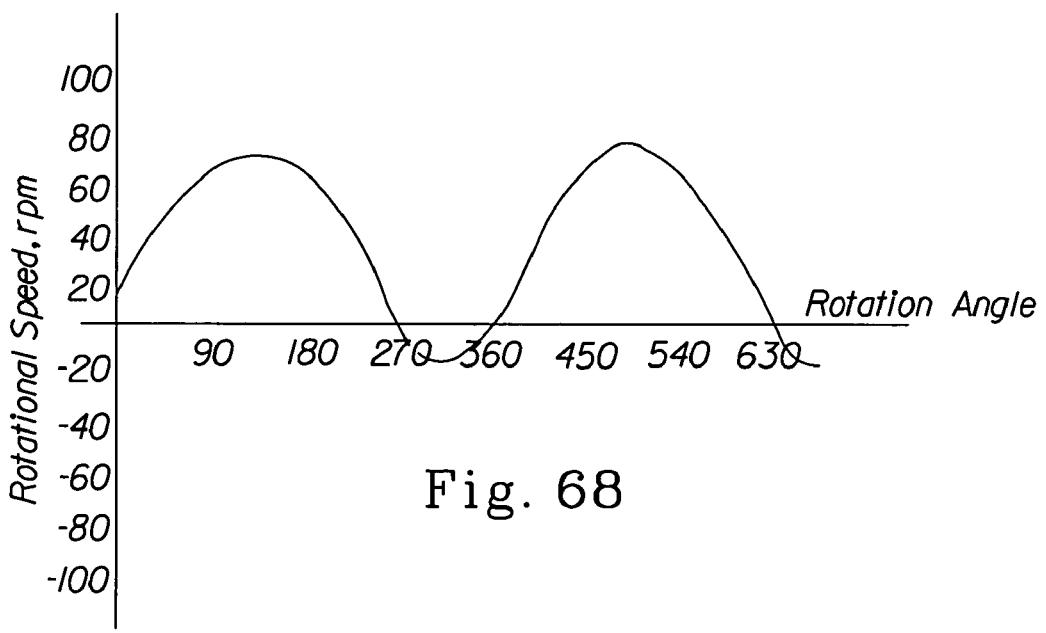

In accordance with certain embodiments, the applicator head is driven in a rotating oscillation movement, defined herein as automatic, bidirectional rotation. Accordingly, the applicator head 20 alternates between forward and reverse rotation upon actuation of the switch 24. Both the forward and reverse rotation may be performed at a static speed or a dynamic speed, as with the single direction rotation described above. In addition, the forward and reverse rotational speeds may be different. For example, the reverse rotational speed may be relatively slower to facilitating transfer of cosmetic from the applicator head 20 to the keratinous fibers, while the forward rotational speed may be relatively faster to promote separation of the keratinous fibers. FIG. 67 shows a graph illustrating uniform acceleration between forward and reverse directions with respect to the rotation angle of the stem. In this graph, the maximum forward and reverse rotational speeds are substantially the same. FIG. 68 in a graph showing a gradually, sinusoidal acceleration between forward and reverse rotational directions, where the maximum forward speed is greater than the maximum reverse speed.

The stem may be rotated in the forward and reverse directions during the same or different periods of time. For example, the forward and reverse rotations may each take place for approximately 1 second. Alternatively, the stem may be rotated in the forward direction for approximately 2 seconds and in the reverse direction for approximately 0.5 seconds. The foregoing time periods are merely exemplary and are provided for clarity of understanding only, as it will be appreciated that other time periods may be used, whether the forward rotation period is greater than, less than, or equal to the reverse rotation period, without departing from the scope of this disclosure.

Figure 69:
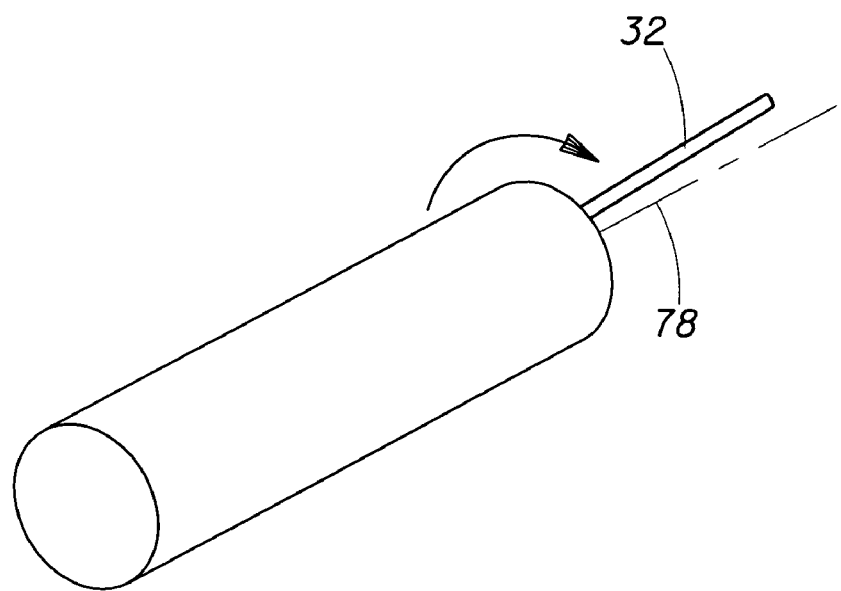
FIG. 69 is a perspective view of an applicator having an offset stem.
Figure 70:
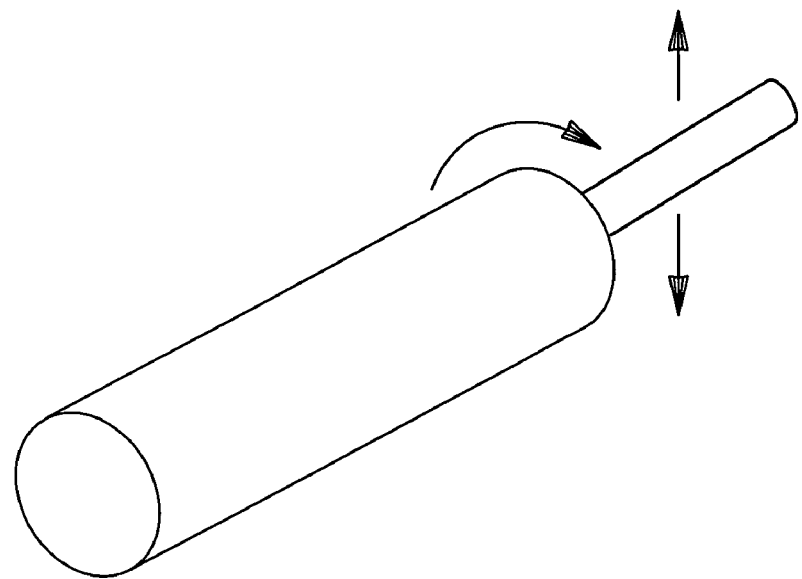
FIG. 70 is a perspective view of an applicator having a stem with a non-uniform cross-sectional shape.

The applicator 10 may produce an applicator head motion that simultaneously rotates and translates about an axis of rotation. As illustrated in FIG. 69, for example, the stem axis 32 may be offset from an axis of rotation 78, so that the stem 16 translates in a circular path as it rotates. Alternatively, the stem 16 may have a non-uniform cross section, such as an oval shape, that causes the stem surface to translate with respect to the lashes as the stem rotates, as shown in FIG. 70.

Various types of actuators may be used to operate the applicator 10. For example, a mechanical device for storing potential energy, such as a spring or twisted rubber band, may be coupled to the stem 16 for producing rotational movement. Alternatively, an electrical device such as the motor 18 may be powered by a battery 22 to rotate the stem 16. The battery may be provided in the handle housing 14 as illustrated in FIG. 1 or may be provided in an associated container of mascara. The container may be keyed to the applicator such that the battery powers the applicator only when a particular mascara container is used. The battery may be rechargeable, and may be provided with or without a charging station.

Figure 71:
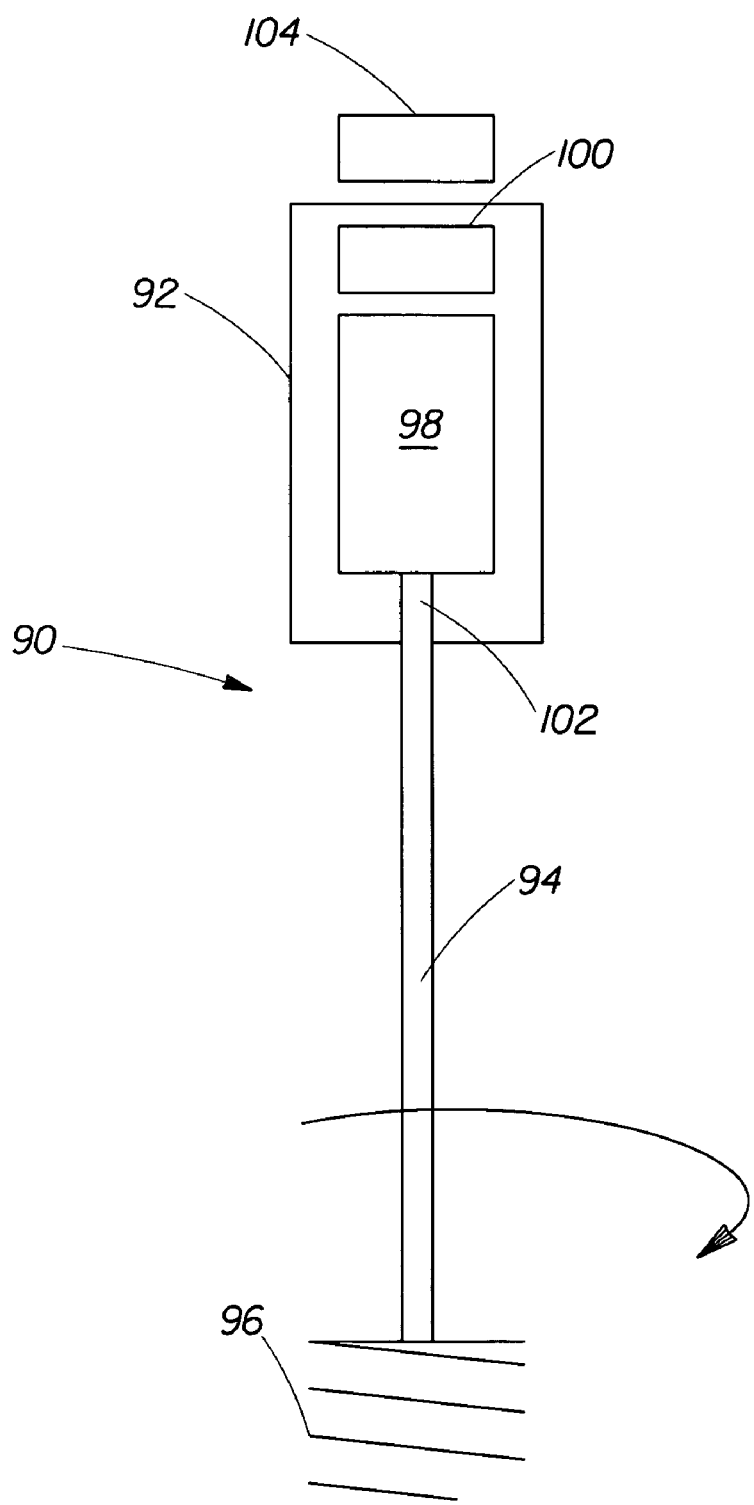
FIG. 71 is a schematic side elevation view, in cross-section, of an applicator having an electric motor.

Some examples of applicators capable of producing rotational applicator head movement will now be described. An applicator 90 capable of simple rotation in one or both directions is schematically illustrated in FIG. 71. The applicator 90 includes a handle 92, a stem 94, and an applicator head 96. A motor 98 and power source, such as a battery 100, are disposed inside the handle. When powered, the motor 98 rotates a motor shaft 102 in a single direction, however the motor may be reversible to selectively rotate the motor shaft 102 in an opposite direction. In the illustrated embodiment, the stem 94 is directly coupled to the motor shaft 102 so that it rotates in the same direction as the rotation of the motor shaft 102 at a 1 to 1 ratio. Alternatively, one or more couplings, such as gears, may be provided which may cause the stem 94 to rotate in a direction opposite the rotation of the motor shaft 102. The gears may be sized so that the stem 94 rotates either faster or slower than the motor shaft 102. A switch 104 is operatively coupled to the battery 100 to selectively provide power to the motor. In operation, a user actuates the switch 104 to turn the motor on, thereby causing the applicator head 96 to rotate.

Figure 72:
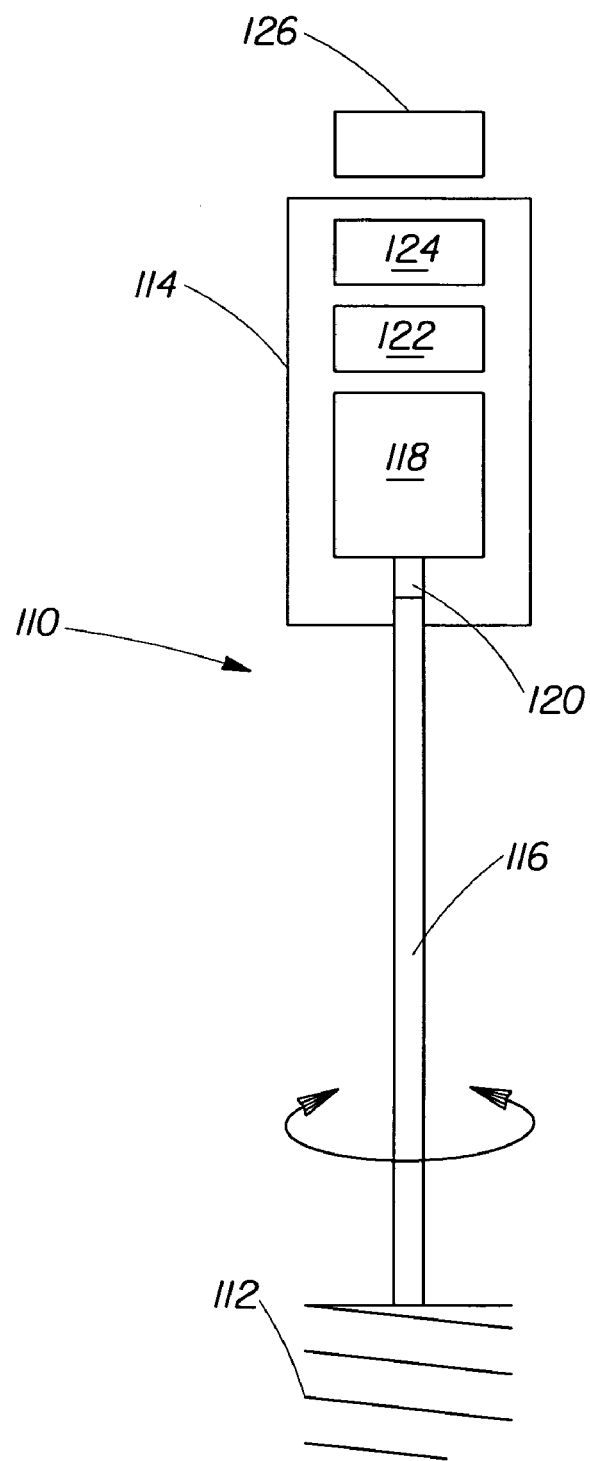
FIG. 72 is a schematic side elevation view, in cross-section, of an applicator having an electric motor and controller.

FIG. 72 illustrates an applicator 110 capable of driving an applicator head 112 in a rotating oscillation movement. The applicator 110 includes a handle 114 and a stem 116 carrying the applicator head 112. An electric motor 118 is disposed in the handle 114 and includes a motor shaft 120 directly coupled to the stem 116. A battery 122 is operatively coupled to the motor 118 and a controller 124 is operatively coupled to the battery 122. A switch 126 is operatively coupled to the controller 124 which, in turn, controls the battery 122 to selectively provide power to the motor 118. The controller 124 may include a timer and may be capable of reversing the polarity of the battery 122, thereby to reverse the direction in which the motor 118 rotates the motor shaft 120. The controller 124 may use the timer to reverse battery polarity at specific times or after predetermined periods of time, thereby to automatically oscillate stem rotation at pre-set frequencies.

Figure 74A:
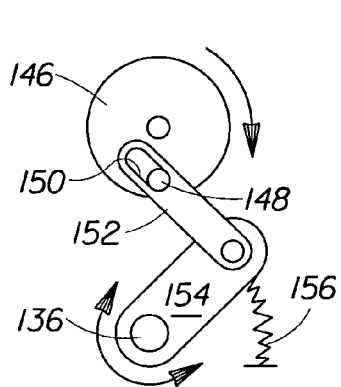
FIGS. 74A-D are partial schematic side elevation views of the transmission coupling of FIG. 73 in various stages of operation.
Figure 74B:
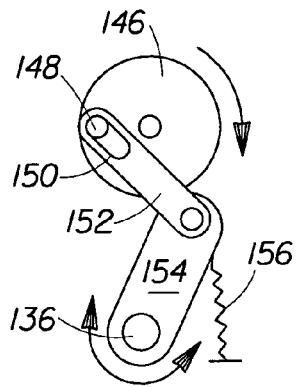
Figure 74C:
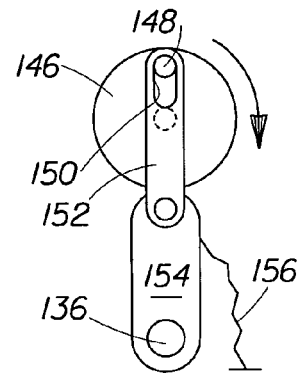
Figure 74D:
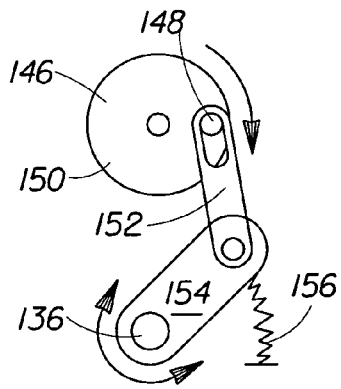
Figure 73:
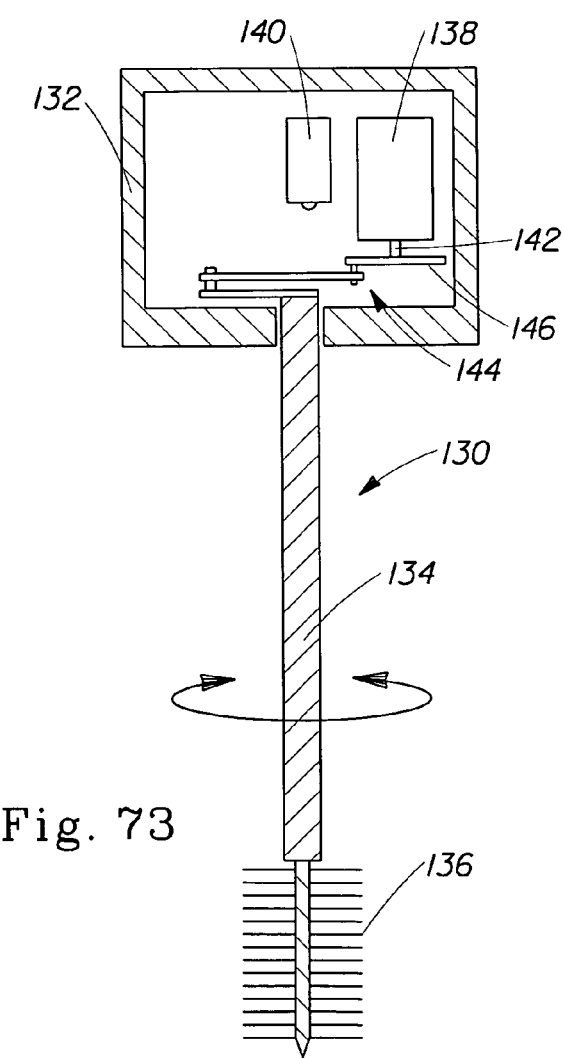
FIG. 73 is a schematic side elevation view, in cross-section, of an applicator having a transmission coupling for converting a uni-directional motor rotation into a rotating oscillation movement of an applicator head.

Another applicator 130 is illustrated in FIGS. 73 and 74A-D in which motor rotation in a single direction is converted into a rotating oscillation motion. The applicator 130 includes a handle 132, a stem 134, and an applicator head 136. A motor 138 and battery 140 are operatively coupled together and disposed inside the handle 132. The motor 138 includes a motor shaft 142 that is mechanically coupled to the stem 134 by a transmission coupling 144. More specifically, the transmission coupling 144 includes a motor disc 146 coupled to the rotating motor shaft 92. The motor disc 146 includes a pin 148 sized for insertion into a slot 150 formed in a connecting rod 152. The connecting rod 152 is pivotably coupled to a first end of an idler rod 154. A second end of the idler rod 154 is fixed to the stem 134, so that the idler rod 154 and stem 134 rotate together. A spring 156 extends between the handle 132 and the idler rod 154 to bias the idler rod 154 in a first direction. In operation, the pin 148 may first be positioned adjacent a lower end of the slot 150 as shown in FIG. 74A. As the motor disc 146 rotates clockwise, the pin 148 moves from the lower end to the upper end of the slot 150, as shown in FIG. 74B. As the pin 148 continues to rotate upwardly, the connecting rod 152 and idler rod 154 are pulled in a vertically upward direction illustrated in FIG. 74C, thereby causing a counter-clockwise rotation of the stem 134. From the position shown in FIG. 74C, further rotation of the motor disc 146 moves the pin 148 downwardly to slide from the upper end to the lower end of the slot 150, as shown in FIG. 74D. Further rotation of the motor disc 146 drives the connecting rod 152 and idler rod 154 downwardly back to the position shown in FIG. 74A, thereby to rotate the stem 134 in a clockwise direction. Accordingly, the transmission coupling 144 converts uni-directional rotation of the motor shaft 142 into a rotating oscillation of the stem 134.

Figure 75A:
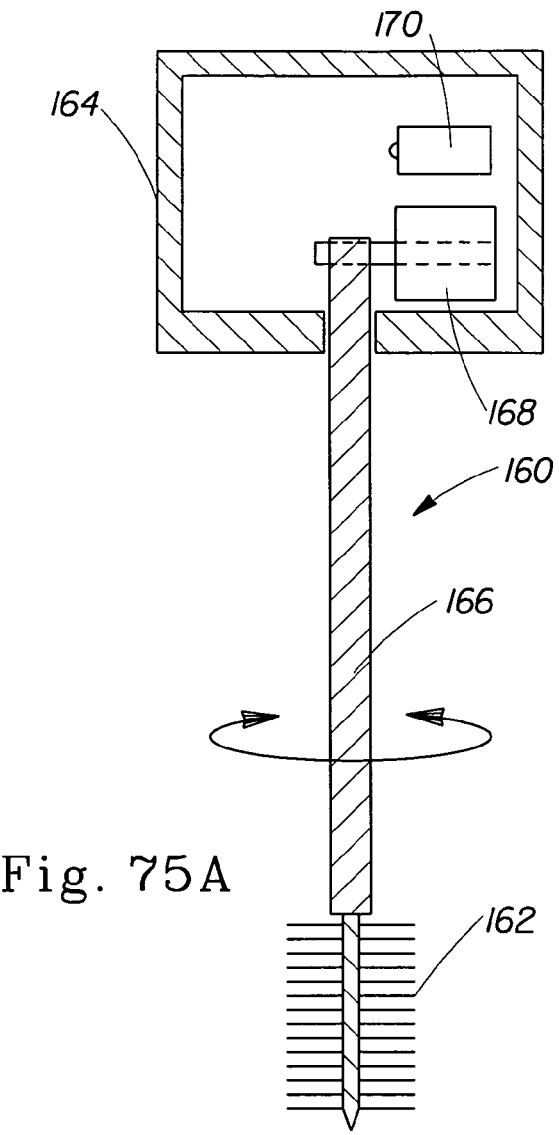
FIGS. 75A-C are schematic side elevation views, in cross-section, of an applicator having a transmission coupling for converting an axial actuator motion into a rotating oscillation movement of an applicator head.
Figure 75B:
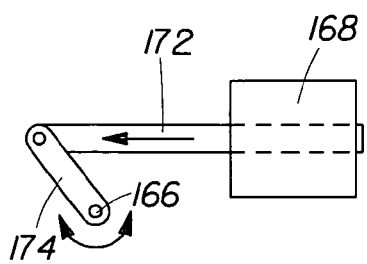
Figure 75C:
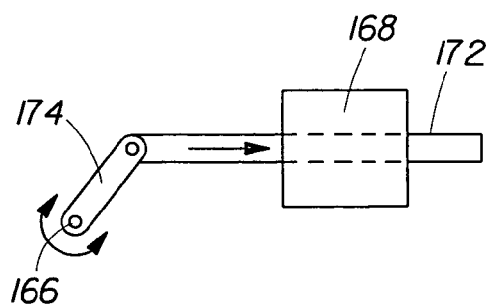

Another exemplary embodiment of an applicator 160 capable of driving an applicator head 162 in a rotational movement is illustrated in FIGS. 75A-C. The applicator 160 includes a handle 164 and a stem 166 carrying the applicator head 162. An electrical coil actuator 168 and battery 170 are disposed in the handle 164 and operatively coupled together. The coil actuator 168 reciprocates a drive shaft 172 along an axis of the shaft 172. The drive shaft 172 is pivotably coupled to a first end of an idler shaft 174. A second end of the idler shaft 174 is fixed to and rotates with the stem 166. In operation, the actuator 168 reciprocates the drive shaft 172 between extended and retracted positions, illustrated in FIGS. 75B and 75C, respectively. As the drive shaft 172 moves from the extended position to the retracted position, the idler shaft 174 and attached stem 166 are rotated in a clockwise direction. When the drive shaft 172 moves in the reverse direction from the retracted position to the extended position, the idler shaft 174 and stem 166 are rotated in the counter-clockwise direction. The speed of rotation and time periods during which the stem 166 is rotated in the forward and reverse directions may be determined by the coil actuator 168, the battery 170, and/or a controller (not shown).

Figure 76A:
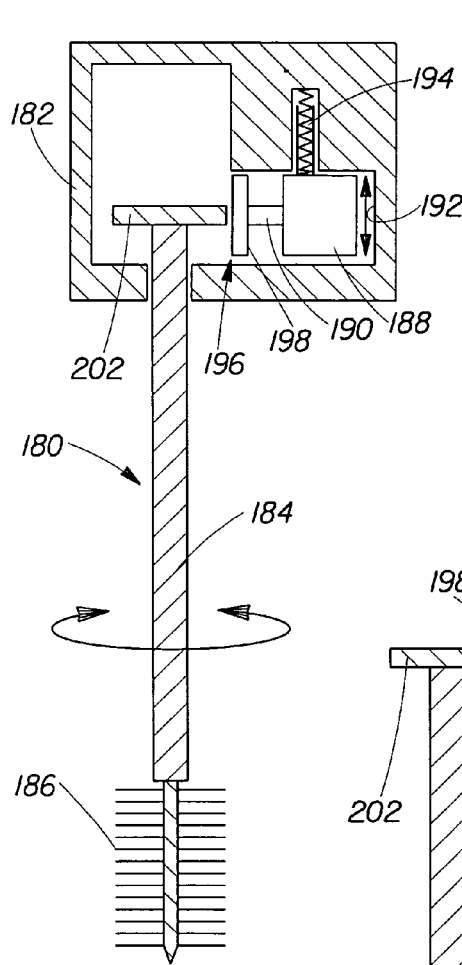
FIGS. 76A-D are schematic side elevation views of an applicator having a transmission coupling for converting a uni-directional motor rotation into a rotating oscillation movement of an applicator head.
Figure 76B:
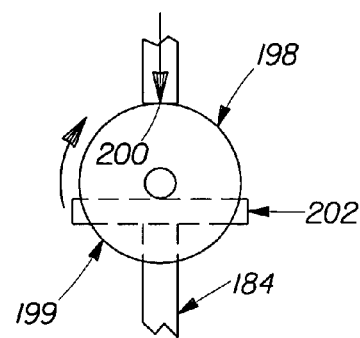
Figure 76C:
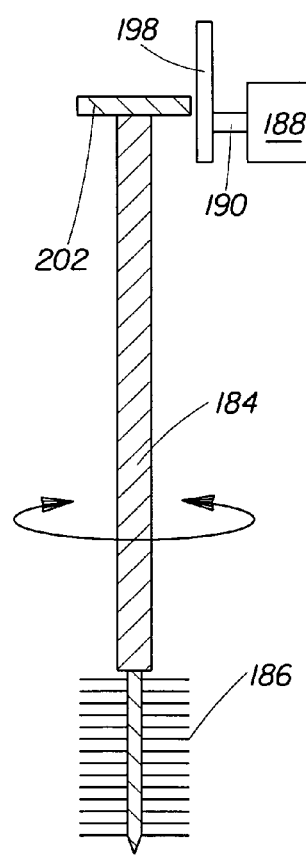
Figure 76D:
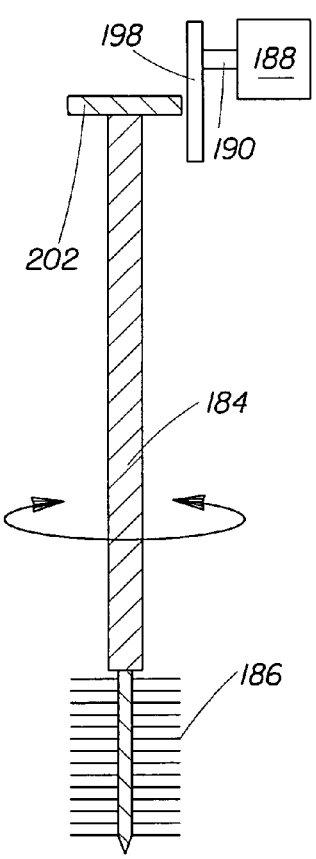

Another further exemplary embodiment of an applicator 180 is illustrated in FIGS. 76A-D. The applicator 180 includes a handle 182 and a stem 184 carrying an applicator head 186. As shown in FIG. 76A, a motor 188 having a rotating motor shaft 190 is disposed in an oversized cavity 192 formed in the handle 182 and is biased toward a downward position by a spring 194. A transmission coupling 196 is provided to operably couple the motor shaft 190 to the stem 184. The transmission coupling 194 includes a motor disc 198 having an oblong shape defining a cam surface 199, as best shown in FIG. 76B, and engages a fixed surface 200 in the handle 182 to provide a cam action as the motor disc 198 rotates. The motor disc 198 frictionally engages a stem disc 202 attached to the stem 184. In operation, the motor 188 rotates the motor disc 190 which drives the stem disc 202. As the motor disc 198 rotates, the motor 188 is driven up and down by the cam action of the motor disc 198 against the fixed surface 200. The center of rotation of the motor disc 198 therefore moves above and below the elevation of the stem disc 202. When the center of motor disc rotation is above the elevation of the stem disc 202 as shown in FIG. 76D, the stem 184 is rotated in a clockwise direction. Conversely, when the center of motor disc rotation is below the elevation of the stem disc 202 as shown in FIG. 76C, the stem 184 is rotated in a counter-clockwise direction. It will be appreciated that as the center of motor disc rotation moves farther away from the elevation of the stem disc 202, the stem disc is rotated at a faster speed. Accordingly, the transmission coupling 196 converts a uni-directional motor rotation into a rotating oscillation of the stem in which the speed of rotation varies in both the forward and reverse rotation directions.

Figure 77:
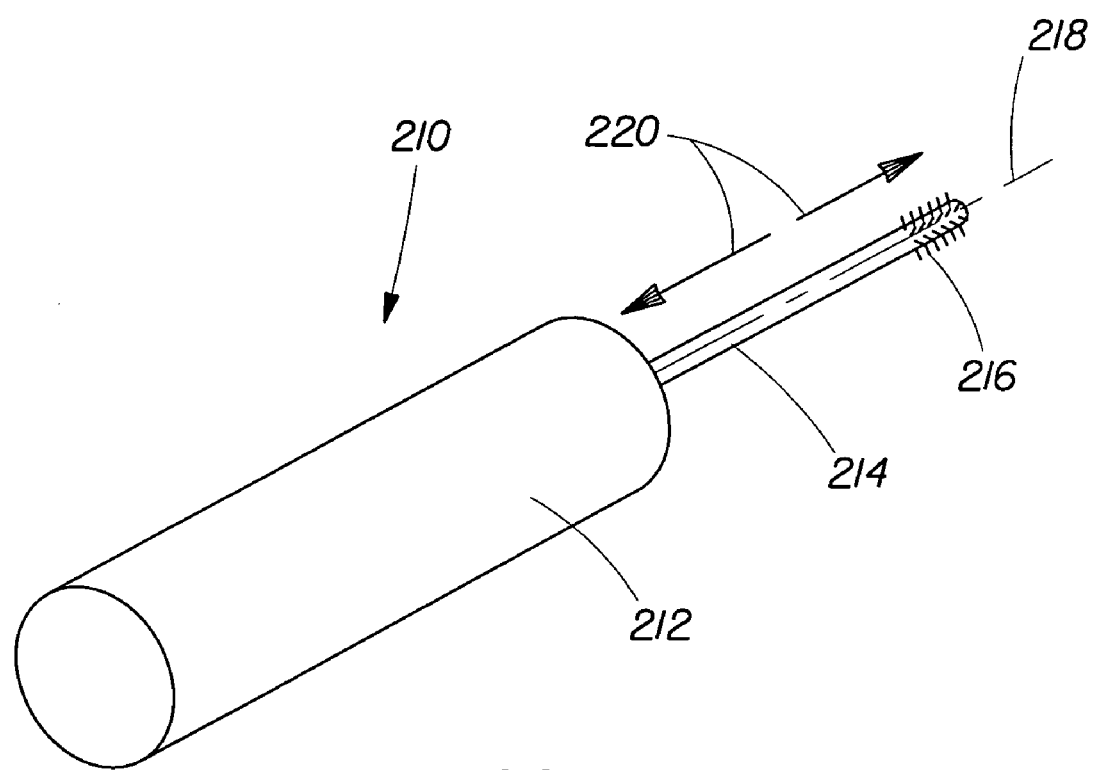
FIG. 77 is a perspective view of an applicator having an applicator head with an axial movement.

It is also advantageous to provide an applicator capable of producing axial translation of the applicator head to assist with eyelash coverage, separation, or other function associated with the application of mascara to eyelashes. FIG. 77 illustrates an applicator 210 having a handle 212 and a stem 214 carrying an applicator head 216. A power source, such as the mechanical or electrical power sources described above, may be disposed in the handle 212 and coupled to the stem 214 to translate the stem 214 and attached applicator head 216 along an axis 218 of the stem, as indicated by arrows 220 in FIG. 77. Alternatively, the applicator head 216 may be directly coupled to the power source for axial movement while the stem 214 is substantially stationary. In this alternative, some protrusions may be coupled to the stem while other protrusions may be coupled to the head so that the applicator includes a combination of both moving protrusions and relatively stationary protrusions.

The axial motion provided by the applicator 210 may be characterized by the frequency of movement of the applicator head 216, the axial distance traveled by the applicator head 216, and the symmetry of the speed at which the applicator head moves during the forward and reverse components of the axial movement. The frequency of movement is defined as the number of times per second (Hz) that the applicator head 216 moves back and forth through one complete cycle. In general, frequencies of approximately 0.5 to 1000 Hz are desired, with a range of approximately 1 to 300 Hz being preferred and a range of approximately 2 to 200 Hz being most preferred. The distance traveled by the applicator head 216 during the axial movement is defined as the displacement distance between the fully extended and fully retracted positions of the applicator head. In general, a distance of approximately 0.1 to 10 mm is desired, with a range of approximately 0.25 to 8 mm being preferred and a range of approximately 0.5 to 5 mm being most preferred. Axial motion is typically along a line substantially parallel to the stem axis. This is in contrast to vibrational motion, which may be in an axial, radial, orbital or other direction. Also, axial motion typically has a frequency nearer the lower range limits and a displacement distance near the upper range limits, while vibrational motion typically has a higher frequency and lower displacement distance. Despite these differences, many of the embodiments described herein are capable of selectively generating both axial motion and vibrational motion.

Speed symmetry describes the relative time taken for the forward stroke versus the reverse stroke. In general, it is desirable to have the ratio of the forward stroke speed to the reverse stroke speed within the range of approximately 1:10 to 10:1, with a range of approximately 1:3 to 3:1 being preferred and a range of approximately 1:2 to 2:1 being most preferred.

A more complex axial motion may be achieved by pausing the motion at any point during the cycle. For example, the axial motion may momentarily stop at the ends of both a forward stroke and a reverse stroke. The period during which the motion is stopped may range from being almost instantaneous to an appreciable delay, particularly when compared to the time it takes to complete a forward or reverse stroke. The time period during which the axial motion is stopped may range from approximately 0.01% to 1000% of the forward or reverse stroke time.

An exemplary embodiment of an applicator 230 capable of producing a composite motion including both rotational and axial oscillation is illustrated in FIGS. 78A and 78B. The applicator 230 includes a handle 232 and a stem 234 carrying an applicator head 236. A coil actuator 238 is disposed in the handle 232 and includes a drive shaft 240. A transmission coupling 242 is provided for operably connecting the stem 234 to the drive shaft 240. Specifically, the transmission coupling 242 includes a stem extension 244 connected to the drive shaft 240 by a flexible coupling 246, which allows rotation of the stem extension 244 with respect to the drive shaft 240. The stem extension 244 includes a spiral groove 248 sized to receive projections 250 coupled to the handle 232. In operation, the coil actuator 238 reciprocates the drive shaft 240 along a vertical direction between retracted and extended positions, illustrated in FIGS. 78A and 78B, respectively. As the drive shaft 240 moves from the retracted to the extended position, the stem extension 244 is driven downwardly. The groove is forced along the projections 250 to cause the stem to rotate in a clockwise direction when viewed from above. When the drive shaft 240 travels in the upward direction, the stem extension 244 and stem 234 are rotated in a counter-clockwise direction as the stem 234 travels vertically upward. Accordingly, the transmission coupling 242 simultaneously generates rotating and axial oscillation of the stem 234. It should be noted that, for any embodiment producing an axial movement of the stem, similar grooves and projections may be provided to rotate the head as it is driven axially with respect to the handle.

While the foregoing embodiment discloses a simple on/off switch, it will be appreciated that the switch may require continuous pressure from the user to remain in the on position. Furthermore, the switch may be provided as a potentiometer to vary voltage supplied to the motor, thereby to provide a variable applicator head motion.

Figure 79A:
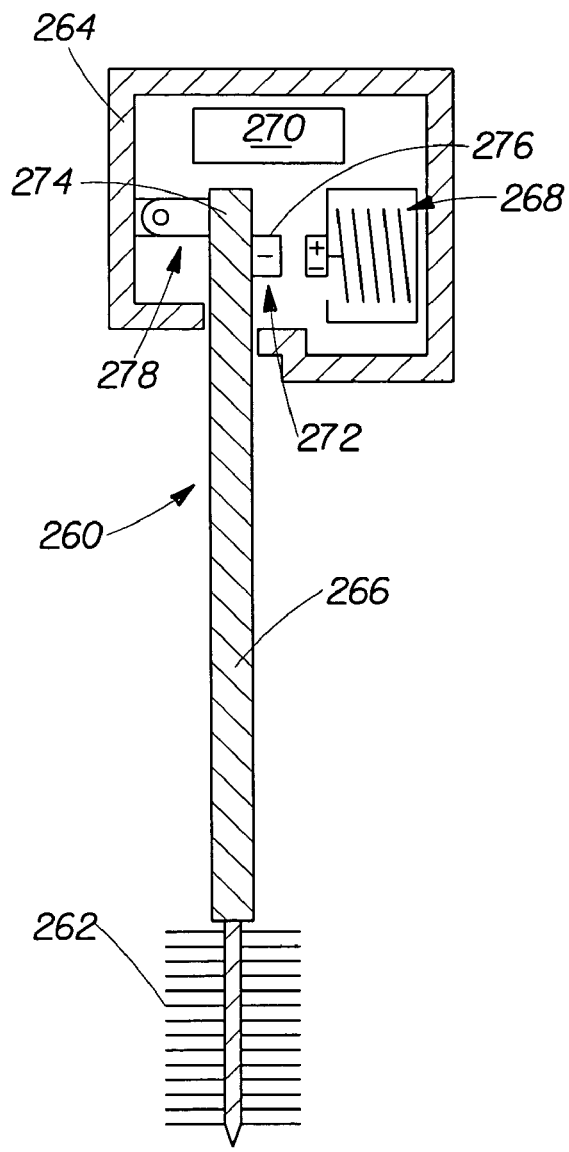
FIGS. 79A-C are schematic side elevation views of an applicator having a transmission coupling for converting electromagnetic potential into axial movement of an applicator head.
Figure 79B:
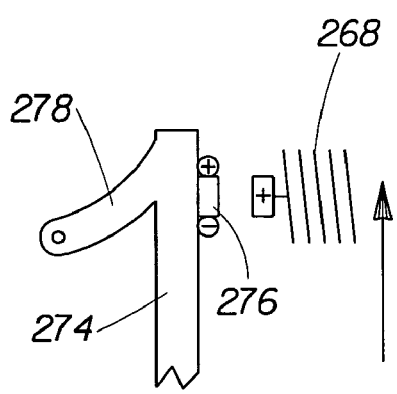
Figure 79C:
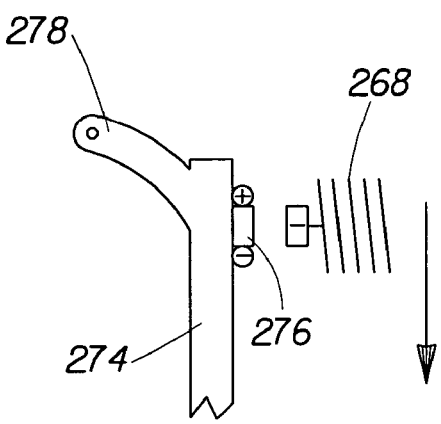

Another exemplary embodiment of an applicator 260 capable of moving an applicator head 262 in an axial direction is illustrated in FIGS. 79A-C. The applicator 260 includes a handle 264 and a stem 266 carrying the applicator head 262.

An alternating current electromagnetic motor 268 and a battery 270 are disposed in the housing and operably coupled to one another. The motor 268 is capable of reversing its polarity. The applicator 260 includes a transmission coupling 272 for generating vibration or axial oscillation of the stem 266. The stem 266 includes an extension portion 274 carrying a polarized magnet 276. A flexible link 278 has a first end coupled to the stem extension portion 274 and a second end pivotably coupled to the handle 264. In operation, the polarity of the motor 268 is reversed to alternate between attracting and repelling the polarized magnet 276, thereby driving the stem extension 274 and attached stem 266 in a vertically reciprocating motion. The amplitude and frequency of the stem's vertical displacement may be controlled to produce either a vertical oscillation (typically characterized by a lower frequency and greater amplitude) or a vibrational motion (typically characterized by a higher frequency and smaller amplitude).

Figures 80A, 80B, 80C, 80D:
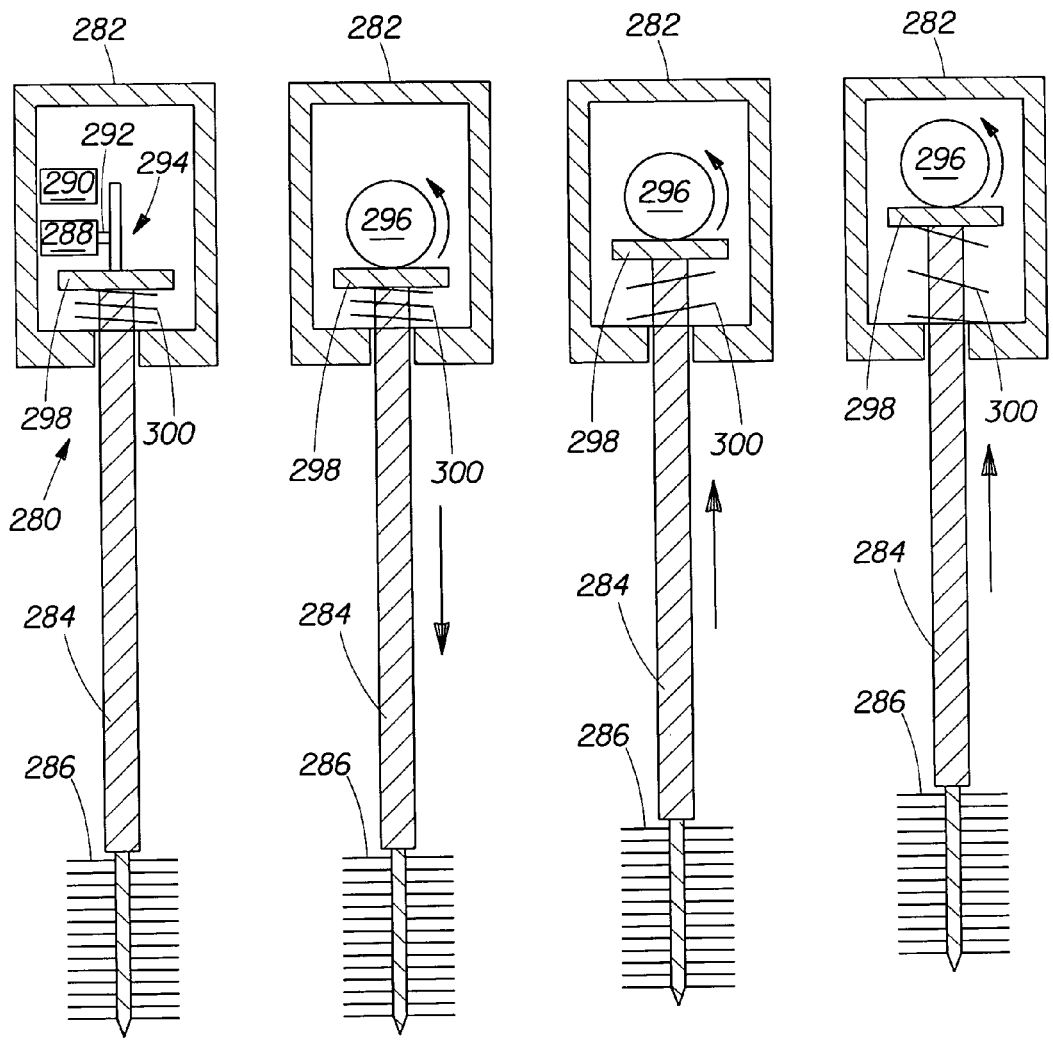
FIGS. 80A-D are schematic side elevation views, in cross-section, of an applicator having a transmission coupling for converting a uni-directional motor rotation into an axial movement of an applicator head.

Yet another exemplary embodiment of an applicator 280 for producing an axial applicator head movement is illustrated in FIGS. 80A-D. The applicator 280 includes a handle 282 and a stem 284 carrying an applicator head 286. A motor 288 and battery 290 are disposed in the handle 282 and are operably coupled to one another. The motor 288 is capable of rotating a motor shaft 292 in at least a first direction. A transmission coupling 294 is provided for operably connecting the motor shaft 292 to the stem 284. The transmission coupling 294 includes a motor cam disc 296 coupled to the motor shaft 292. A stem disc 298 is coupled to an end of the stem 284. A spring 300 biases the stem disc 298 toward an upper position. In operation, the motor cam disc 296 rotates to drive the stem disc 298 downwardly against the force of the spring 300, thereby to push the stem disc 298 and attached stem 284 to a lower position, as shown in FIG. 80B. Further rotation of the motor cam disc 296 allows the spring 300 to push the stem disc 298 upwardly, thereby returning the stem disc 298 and stem 284 to an upper position shown in FIG. 80D. Accordingly, the transmission coupling 294 converts unidirectional rotation of the motor cam disc 296 into bi-directional, axial oscillation of the stem 284. The axial motion of the stem 284 may be either an axial oscillation or a vibration of the stem.

A still further exemplary embodiment of an applicator 310 for producing an axial applicator head motion is illustrated in FIGS. 81A-C. The applicator 310 includes a handle 312 and a stem 314 carrying an applicator head 316. A motor 317 is disposed in the handle 312 and is capable of rotating a motor shaft 318 in at least one direction. A battery 320 is also disposed in the handle 312 and is operatively coupled to the motor 316. A transmission coupling 322 is provided for operatively connecting the motor shaft 318 to the stem 314. The transmission coupling 322 includes a motor disc 324 coupled to the motor shaft 318. The motor disc 324 frictionally engages a stem disc 326 coupled to the stem 314. A cam follower 328 is coupled to the stem disc 326 and shaped to engage a cam driver surface 330 coupled to the handle 312. A spring 332 extends between the handle 312 and the stem disc 326 to bias the stem 314 toward an upper position. In operation, rotation of the motor disc 324 rotates the stem disc 326. As the stem disc 326 rotates, the cam follower 328 slides along the cam driver surface 330 to simultaneously push the stem disc 326 downwardly against the force of the spring 332. As a result, the elevation of the stem disc 326 moves above and below a center of rotation of the motor disc 324 as it rotates. When the center of motor disc rotation is above the elevation of the stem disc 326 as shown in FIG. 81B, the stem 314 is rotated in a clockwise direction. Conversely, when the center of motor disc rotation is below the elevation of the stem disc 326 as shown in FIG. 81C, the stem 314 is rotated in a counter-clockwise direction. It will be appreciated that as the center of motor disc rotation moves farther away from the elevation of the stem disc 326, the stem disc is rotated at a faster speed. Accordingly, the transmission coupling 322 converts a uni-directional motor rotation into a rotating oscillation and an axial movement of the stem, in which the speed of rotation varies in both the forward and reverse rotation directions. The axial movement may be either an axial oscillation or a vibration of the stem.

Figure 88:
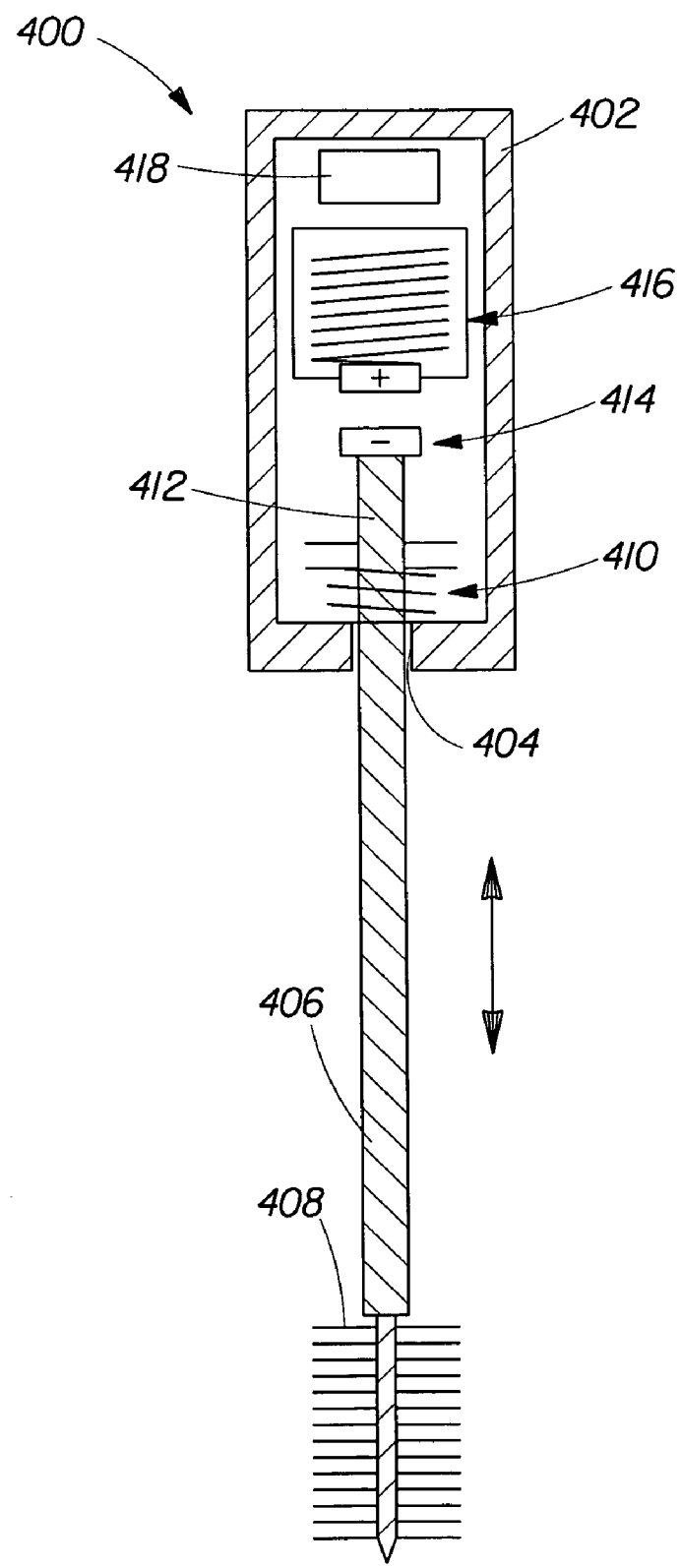
FIG. 88 is a schematic side elevation view, in cross-section, of an applicator capable of vibrating an applicator head.

An applicator 400 particularly suited to generate a vibrating applicator head is illustrated at FIG. 88. The applicator 400 includes a handle 402 having an orifice 404 sized to slidingly receive a stem 406 capable of moving between extended and retracted positions and carrying an applicator head 408. A spring 410 biases the stem 406 in one of the extended or retracted positions. A stem extension 412 includes a magnet 414. An actuator in the form of an electromagnetic coil 416 is disposed in the handle 402 and is operably coupled to a battery 418. The coil 416 may be selectively energized to produce a magnetic field that either attracts or repels the magnet 414 on the stem extension 412, thereby to move the stem 406 between extended and retracted positions, thereby reciprocating the applicator head 408 in a vibrational motion. As an alternative, the actuator may be provided as a piezoelectric diaphragm to generate the vibratory force, rather than the electromagnetic coil 416. Should such a diaphragm be used, the magnet 414 may be removed.

Figure 89:
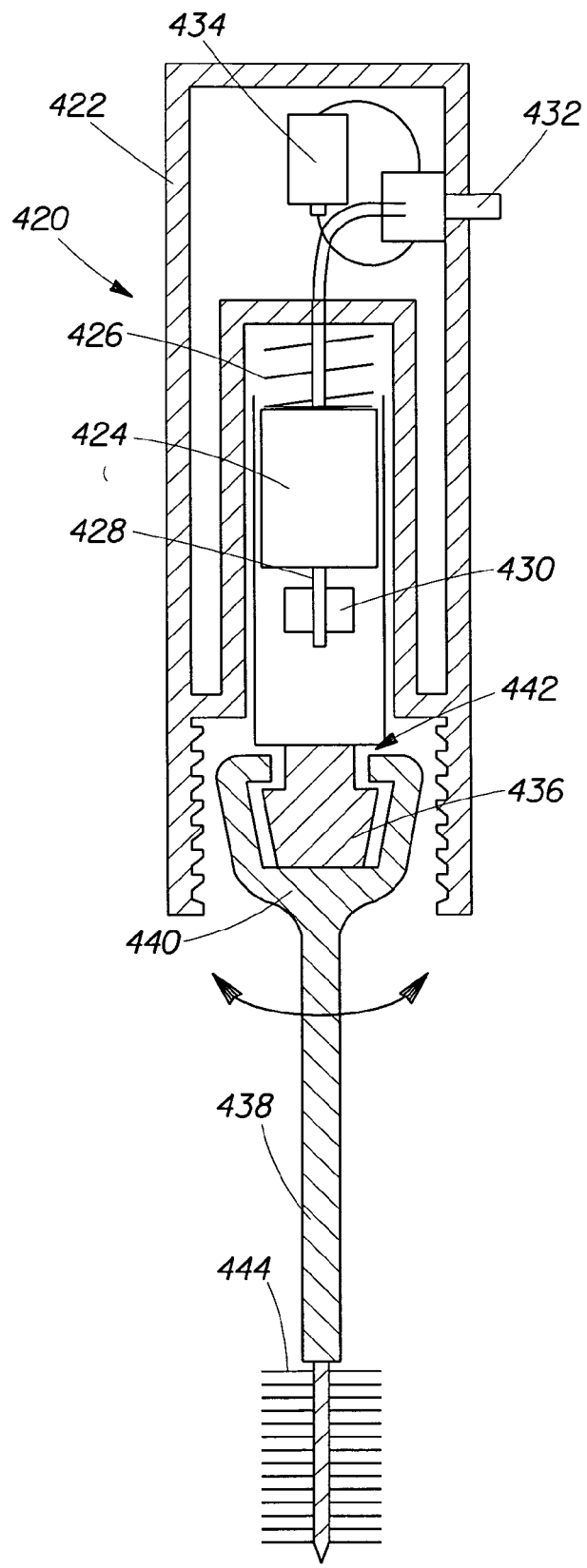
FIG. 89 is a schematic side elevation view, in cross-section, of an applicator capable of moving an applicator head in a composite motion including a vibrational component and a rotational component.

An applicator 420 capable of producing a composite vibrational and rotational motion is illustrated at FIG. 89. The applicator 420 includes a handle 422 with a motor 424 coupled thereto through an isolation spring 426. The motor has a rotating motor shaft 428 with a weight 430 mounted eccentrically with respect to an axis of the motor shaft. A switch 432 and battery 434 are operatively coupled to the motor 424. A boss 436, which may have a generally cylindrical or frusto-conical shape, is also coupled to the handle 422: A stem 438 includes a stem extension 440 defining a socket 442 sized to rotatably engage the boss 436. The stem 438 also carries an applicator head 444. In operation, the rotating eccentric weight 430 generates a vibratory force that is substantially isolated from the handle 422 by the spring 426. The force is transferred via the boss 436 to the stem 438, which causes the stem to rotate. In this embodiment, where the motor shaft 428 is substantially parallel to the stem axis, rotation of the motor shaft 428 in one direction causes rotation of the stem 438 in the opposite direction. The direction of motor shaft rotation may be reversed by switching the polarity of the battery 434. Accordingly, the applicator 420 is capable of moving the applicator head 444 in a composite motion including both a vibrational element and a rotational element.

Figure 90:
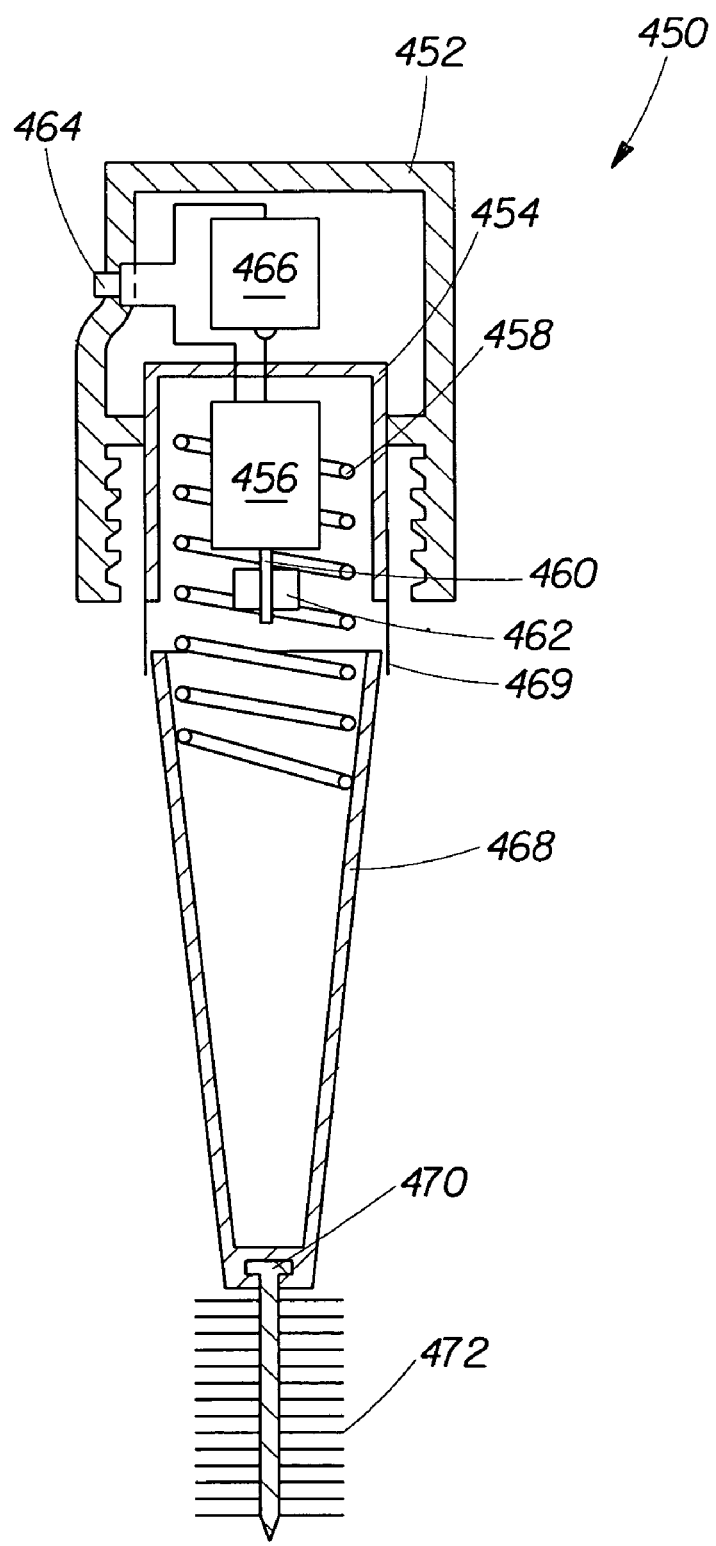
FIG. 90 is a schematic side elevation view, in cross-section, of an applicator capable of moving an applicator head in a composite motion including a vibrational component, a radially translating component, and/or a rotational component.

An applicator 450 capable of producing a composite applicator head motion including one or more vibrational, radial, and rotational components is illustrated in FIG. 90. The applicator 450 includes a handle 452 with an inner sleeve 454 coupled thereto. A motor 456 is supported inside the inner sleeve 454 by a spring 458. The motor 456 includes a rotating shaft 460 and an eccentrically mounted weight 462 coupled thereto. A switch 464 and a battery 466 are operably coupled to the motor 456. A hollow stem 468 is sized to receive a free end of the spring 458. The stem 468 includes a socket 470 sized to rotatably receive an applicator head 472, so that the applicator head 472 is free to rotate with respect to the stem 468. A shroud 469 may be provided to enclose a gap between opposing ends of the inner sleeve 454 and the stem 468. In operation, rotation of the motor 456 generates a rotational force that is isolated from the handle 452 by one end of the spring 458 and transferred to the stem 468 by the other end of the spring 458. The spring 458 allows the stem 468 to radially translated (i.e., to move in a circular path with respect to the inner sleeve 454 without rotating). The applicator head 472, in turn, is free to rotate with respect to the stem 468. As a result, the applicator 450 is capable of moving the applicator head 472 in a composite motion including a radial translation component, a vibrational component, and/or a rotational component.

In the embodiments illustrated in FIGS. 89 and 90, the spring, motor, and eccentric weight may be selected to produce a desired frequency and amplitude for the applicator head motion. The spring may be matched to the motor and weight so that it is energized at or near its natural frequency. When so matched, the motor force is amplified by the spring and delivered to the applicator head, thereby reducing the power required by the motor to produce a given displacement of the applicator head.

Figure 93:
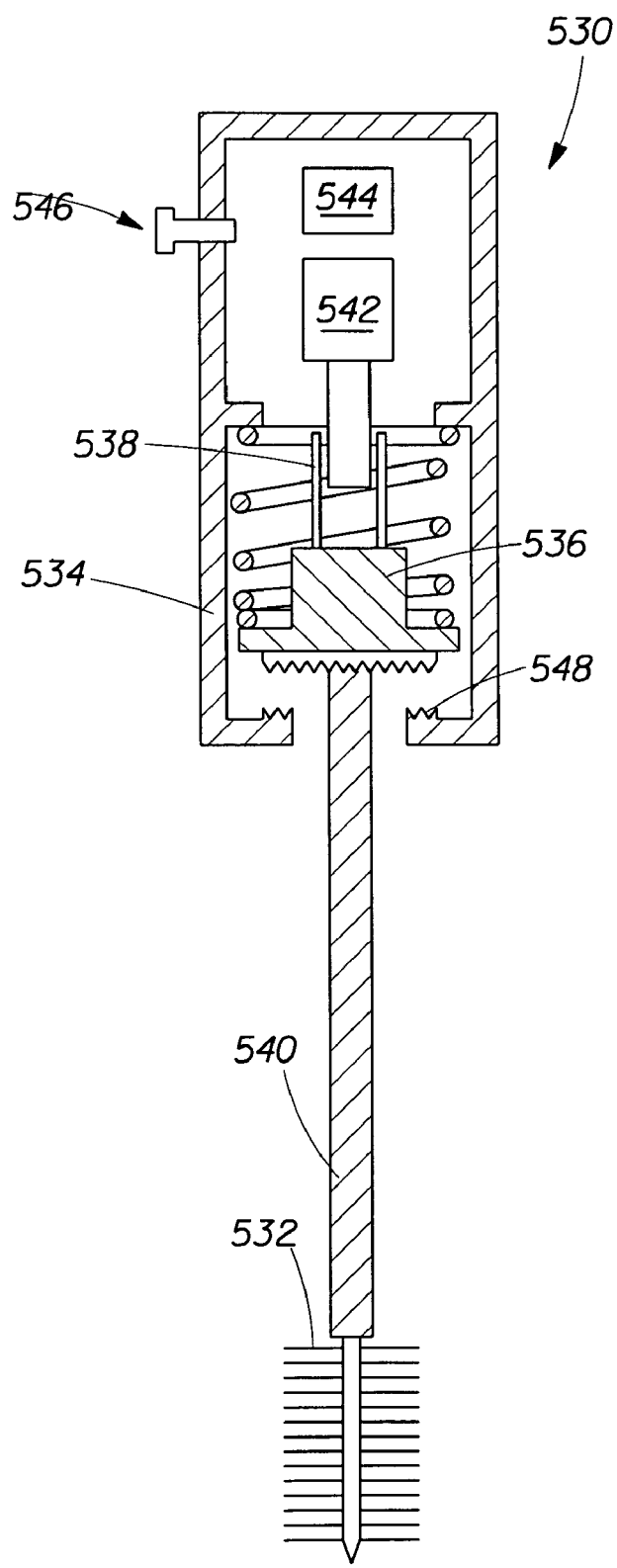
FIG. 93 is a schematic side elevation view, in cross-section, of an applicator capable of moving an applicator head with a vibrational motion and of generating a tactile vibration in the handle.

FIG. 93 illustrates another applicator 530 for moving an applicator head 532 in a vibrational motion. The applicator 530 includes a handle 534. A toothed cam 536 is disposed in the housing and includes a sleeve 538. A stem 540 is coupled to the toothed cam and carries the applicator head 532. A motor 542 includes a rotating shaft coupled to the sleeve 538. A battery 544 and switch 546 are disposed in the handle 534 and operatively coupled to the motor 542. In operation, the motor 542 rotates the cam 536 over teeth 548 formed in the housing to produce a composite applicator head motion having a rotational component and a vibrational component. The vibration is applied to the handle 534 to provide tactile feedback to a user.

Figure 94A:
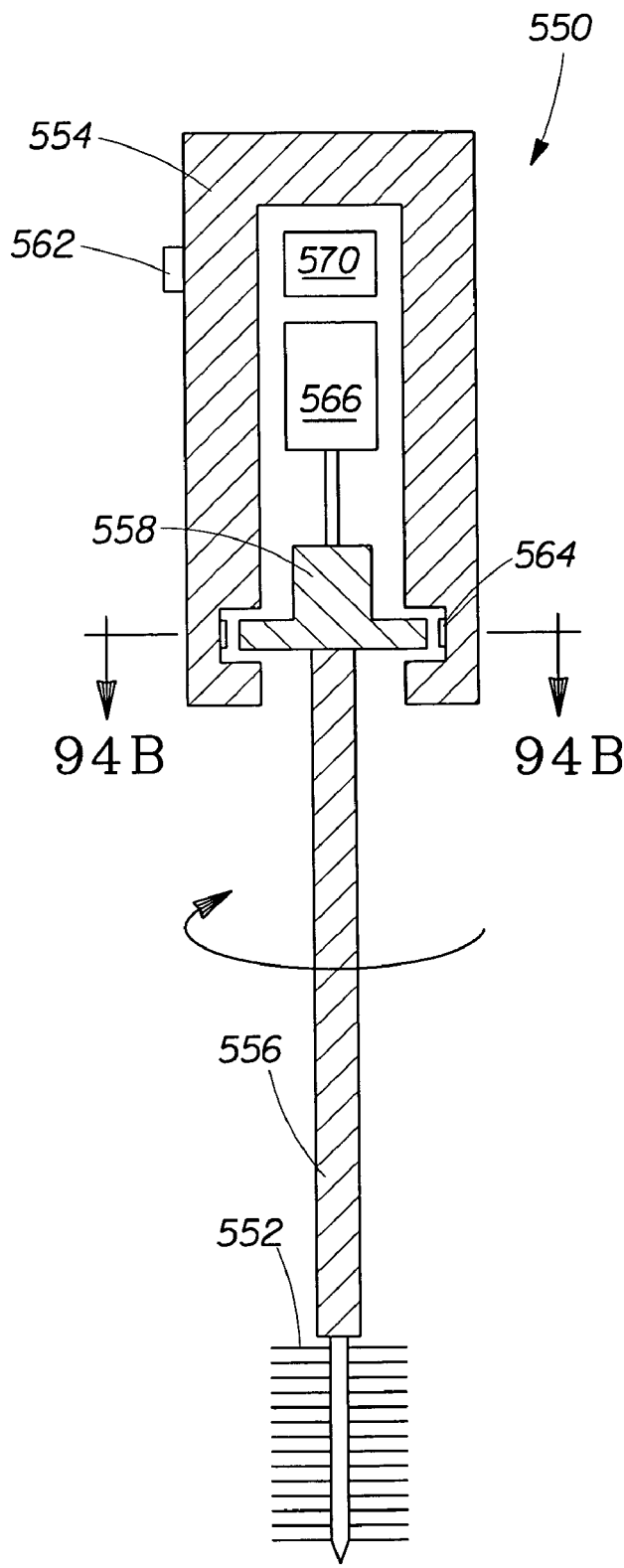
FIGS. 94A and B are schematic views, in cross-section, of an applicator capable of moving an applicator head with a vibrational motion and of generating a tactile vibration in the handle.
Figure 94B:
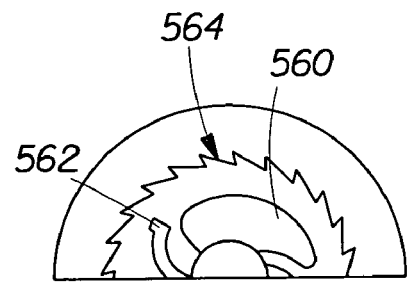

FIGS. 94A and 94B illustrate an applicator 550 for moving an applicator head 552 with rotation and vibration. The applicator 550 includes a handle 554. A stem 556 includes a stem extension 558 includes a stabilizing blades 560 and teeth 562 adapted to engage gear teeth 564 coupled to the handle 554. A motor 566 is coupled to the stem extension 558 and is operatively coupled to a battery 570 and switch 572. In operation, the motor 566 rotates the stem extension 558 to drive the teeth 562 over the gear teeth 564, thereby to generate a vibrational motion of the applicator head 552. The vibration is passed through the handle 554 to provide tactile feedback to a user.

While some of the foregoing embodiments produce a vibrational applicator head movement, any of the applicators described herein may be modified to include a vibration generator to provide sensory feedback to the user. Such a vibration generator may be coupled, either rigidly or resiliently, to the handle for producing a tactile vibration. It has been found that vibrations produced within the range of 10 Hz to 6 kHz can be sensed by the hand of a typical user.

The stems provided in the embodiments disclosed herein may be substantially rigid or substantially flexible as needed. Certain embodiments, such as those having a stem with a groove that engages projections on the housing to transfer axial stem movement into rotational movement, may perform better with a more rigid stem. Other embodiments, such as those that produce a vibrational head motion, may benefit from a more flexible stem. In the embodiments using stems with greater flexibility, a rigid sleeve may be coupled to the housing and extend around at least a portion of the stem to support the stem as desired.

Figure 95:
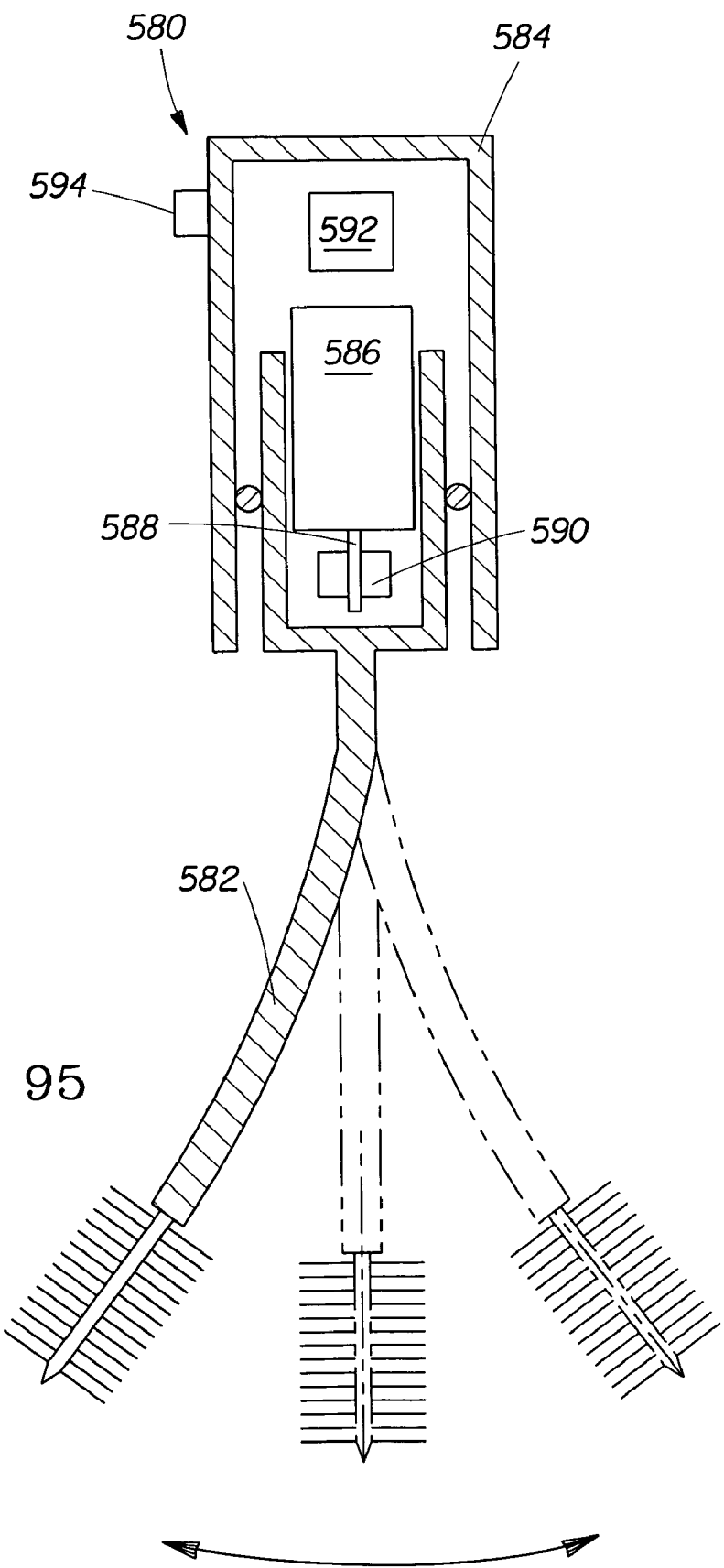
FIG. 95 is a schematic side elevation view, in cross-section, of an applicator having a flexible shaft.
Figure 96:
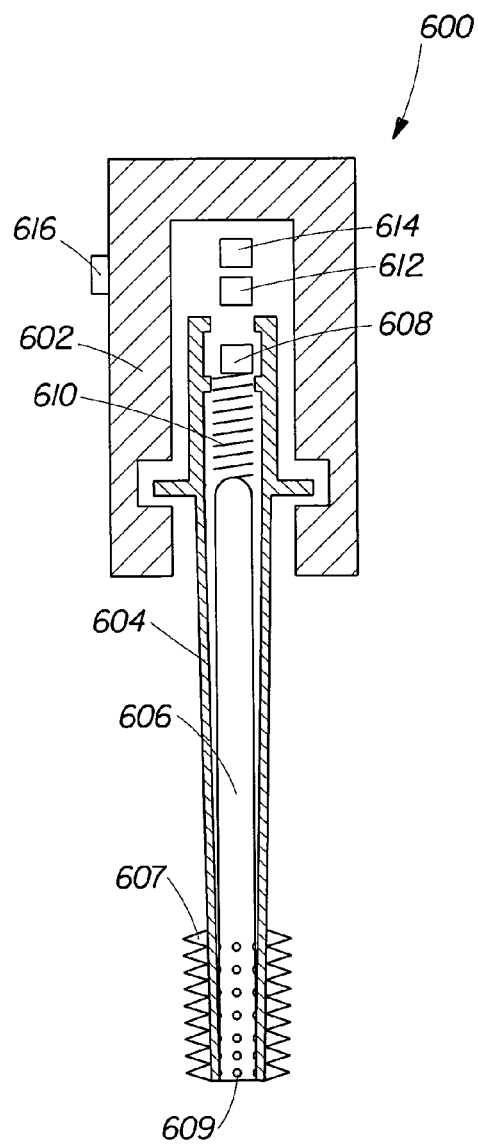
FIG. 96 is a schematic side elevation view, in cross-section, of an applicator having both stationary and moving protrusions.

More specifically, FIG. 95 illustrates an applicator 580 having a flexible stem 582. The applicator includes a handle 584 having a motor 586 with a rotating motor shaft 588. An eccentric weight 590 is mounted on the shaft 588. A battery 592 and switch 594 are operatively coupled to the motor 586. Rotation of the eccentric weight 590 generates a force that is transmitted to the stem 582. The stem 582 is sufficiently flexible to respond to the force by bending back and forth, as shown in FIG. 95. The illustrated stem displacements are exaggerated for clarity of understanding. The stem flexibility may be constant or may vary, such as by a function of cross-sectional area or material density, along the length of the stem 582.

Figure 82A:
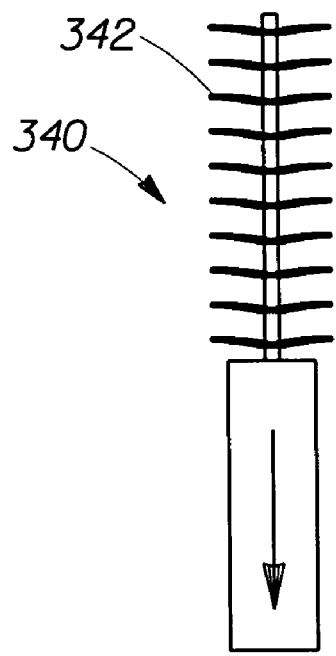
FIGS. 82A and 82B are side elevation views of flexible protrusions on an axially moving applicator head.
Figure 82B:
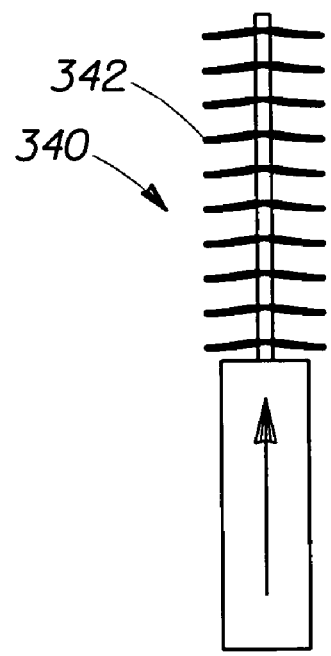

Axial movement of the applicator head may be performed at frequencies which enhance distribution of cosmetic material to the ends of the protrusions. An applicator head 340 may include protrusions 342 that flex in response to axially downward and upward movement, as illustrated in FIGS. 82A and 82B, respectively. The axial movement may be specifically tuned to produce a harmonic motion of the protrusions, thereby more effectively advancing cosmetic material from the base to the tip of each protrusion 342.

Figure 83B:
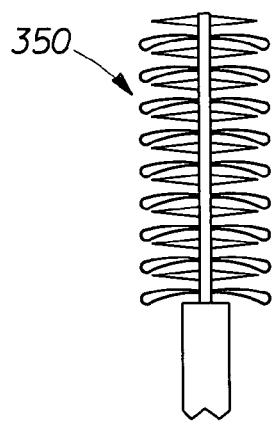
FIGS. 83A-C are side elevation views of a combination of flexible and stiff protrusions on an axially moving applicator head.
Figure 83A:
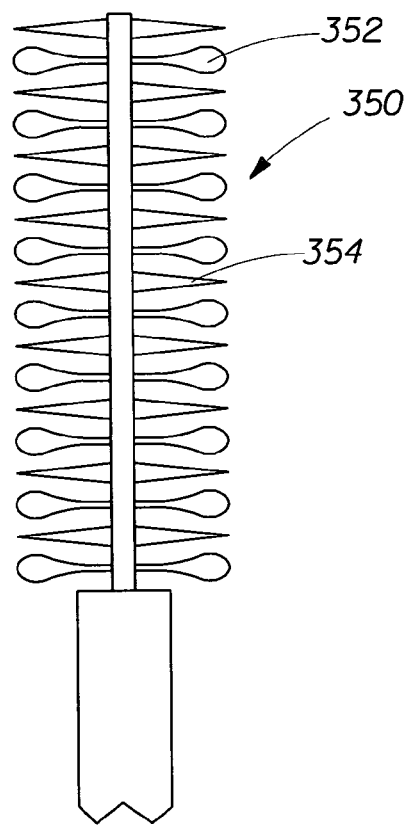
Figure 83C:
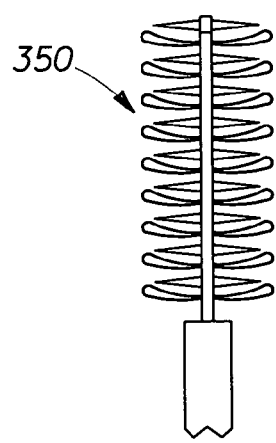

An axially moving applicator head 350 may include protrusions of varying flexibility or stiffness. As illustrated in FIGS. 83A-C, the applicator head 350 includes a first set of protrusions 352 having a relatively low stiffness (or high flexibility) and a second set of protrusions 354 having a relatively high stiffness (or low flexibility). The first set of protrusions 352 will deflect downwardly in response to axial upward movement of the applicator head 350 and upwardly in response to axial downward movement of the applicator head 350, as illustrated in FIGS. 83B and 83C, respectively. In the illustrated embodiment, the first set of protrusions includes more mass at their tips to promote flexibility, while the second set of protrusions are tapered to promote stiffness. Alternatively or additionally, the protrusions may be formed of different materials to create the relative differences in stiffness and/or flexibility.

Figure 84:
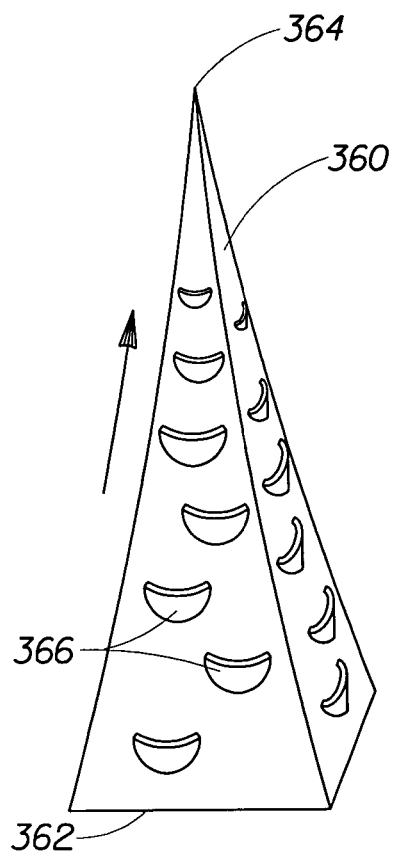
FIGS. 84 and 85 are perspective views of a protrusions formed to promote flow of cosmetic material from a base to a tip.

The shape of each protrusion may also be adapted for use in an axially moving applicator head. FIG. 84 illustrates a protrusion 360 having a generally square base 362. The protrusion gradually tapers from a large cross-sectional area at the base 362 to a small cross-sectional area at the free end or tip 364. A series of recesses, such as dimples 366, are formed in the surface of the protrusion 360 to promote movement of cosmetic product from the base 362 to the tip 364 as the protrusion 360 is vibrated in an axial direction.

Figure 85:
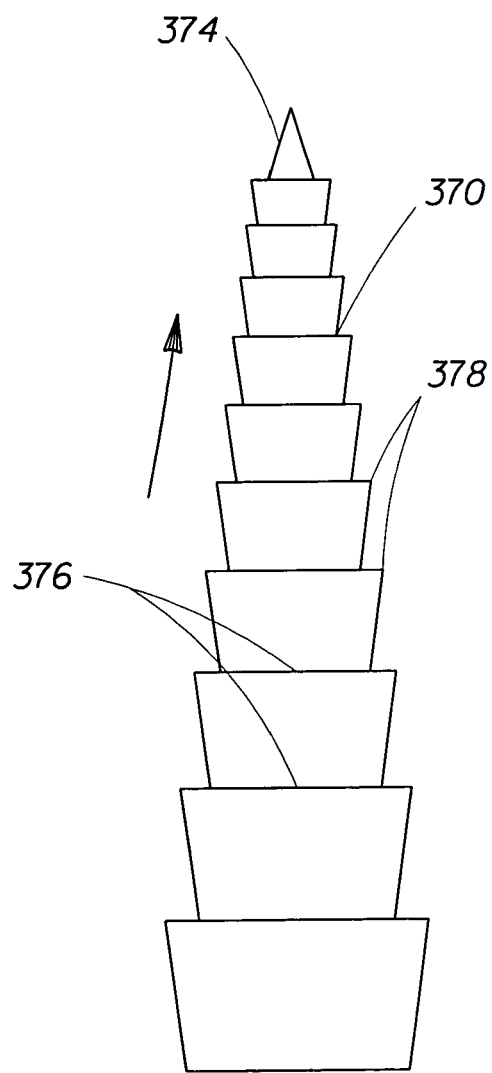

FIG. 85 illustrates another protrusion 370 adapted to facilitate material flow from the base to the tip during axial vibration. The protrusion 370 includes a base 372 having a relatively large cross-sectional area and a tip 374 having a relatively small cross-sectional area. The surface of the protrusion 370 includes a series of tiers 376 to form a terraced profile. The tiers 376 form barb-shaped projections 378 which promote movement of cosmetic from the base 372 to the tip 374 as the protrusion 360 is vibrated in an axial direction.

The applicator may include certain ancillary features to enhance operation or user satisfaction. For example, the applicator may further include a thermal source to apply heat to the applicator head, thereby to promote curl and lift of the lashes. The applicator may include a sound circuit to generate a noise during operation, thereby to alert the user when the applicator is active. Similarly, the applicator may include a secondary vibration source to provide a tactile indication to the user that the applicator is operating, and to potentially enhance the user's perception of the effectiveness of the applicator.

In addition to the electrical and mechanical actuators disclosed herein, the force for applicator head movement may be provided by sound waves. For example, a piezocrystal may be provided for generating sound waves that vibrate the applicator head.

Figure 86:
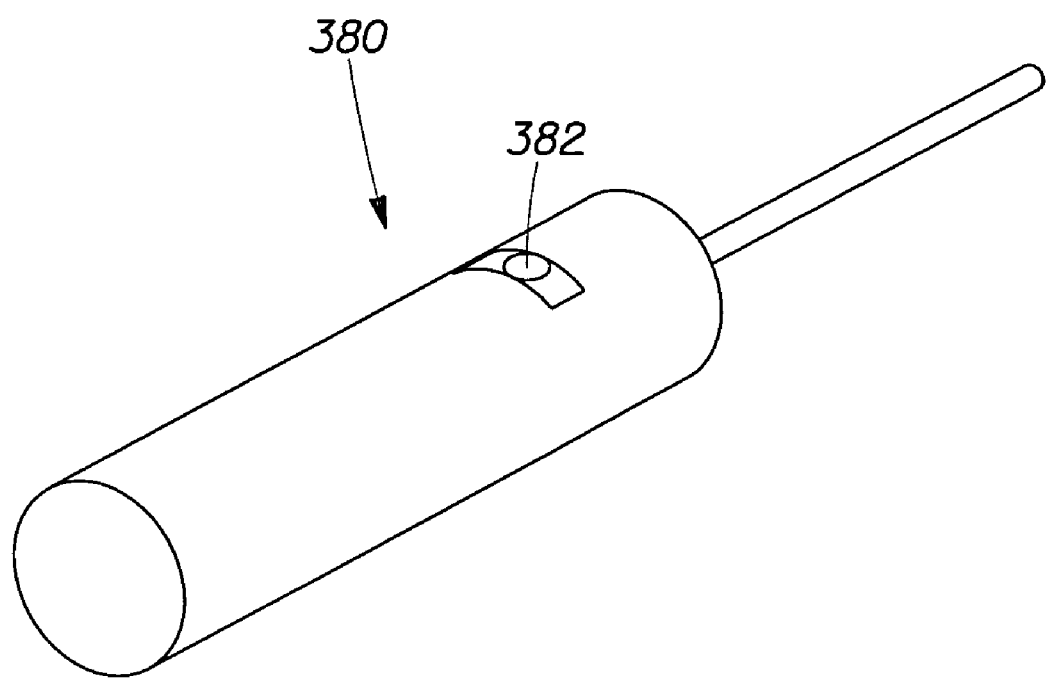
FIG. 86 is a perspective view of an applicator having a switch for reversing rotation of the applicator head.

As illustrated in FIG. 86, an applicator 380 may include a simple toggle control switch 382 to allow quick and easy transition between forward and reverse rotation.

Figure 87:
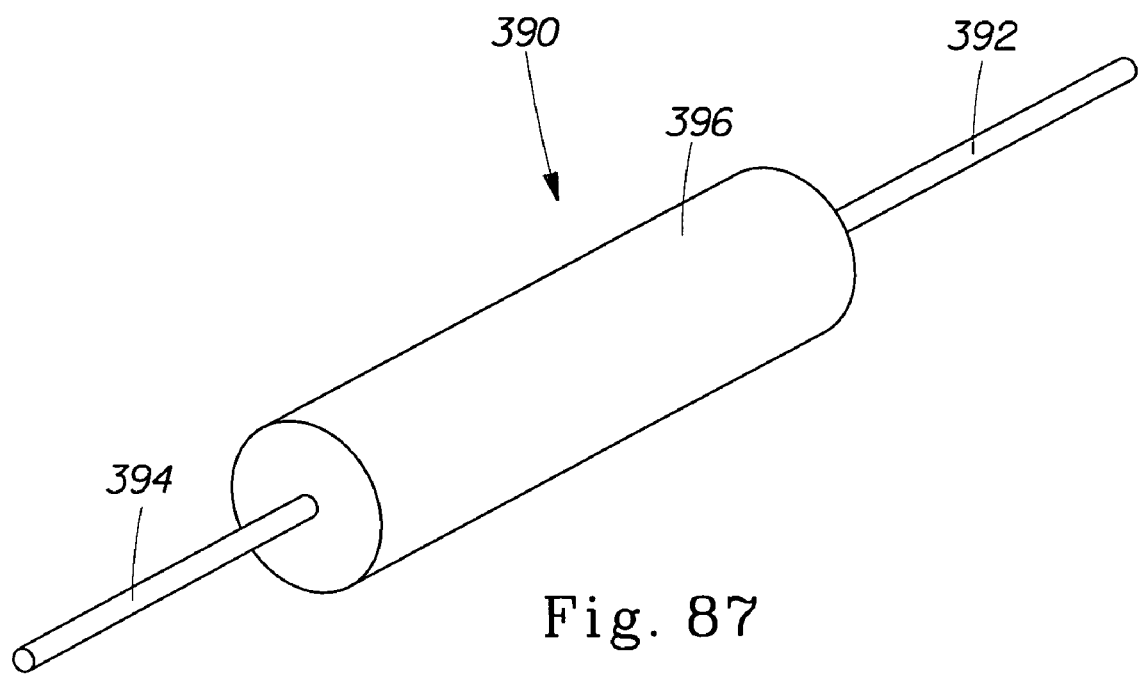
FIG. 87 is a perspective view of an applicator having first and second stems for carrying first and second applicator heads, respectively.

An applicator 390 may include first and second stems 392, 394 extending from opposite ends of a handle 396, as shown in FIG. 87. The same or a different motor may power the second applicator head 394. The second head 394 may have a second, different cosmetic product intended for use either separately or in combination with the cosmetic provided on the first applicator head.

An applicator may have an applicator head or combined applicator head and stem that may be independently removable from the handle to allow a variety of customized applicators to be used with the same handle. The removable head or head/stem combination may include a locking mechanism. The applicator head may further be adapted to provide a combination of both moving (i.e., rotating, axial moving, etc.) and stationary protrusions.

Figure 97A:
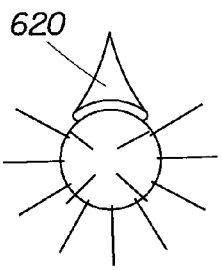
FIGS. 97A-C are plan views, in cross-section, of various embodiments of the applicator of FIG. 96.
Figure 97B:
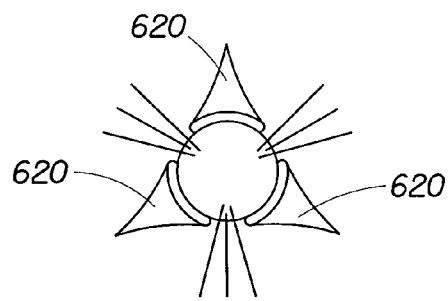
Figure 97C:
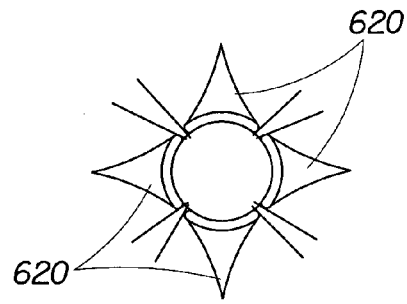

An applicator 600 having stationary and moving protrusions is illustrated in FIGS. 96 and 97A-C. The applicator 600 includes a handle 602. A hollow sleeve 604 is coupled to the handle 602 and a stem 606 is disposed inside the sleeve 604. A first set of protrusions 607 is coupled to the sleeve 604 while a second set of protrusions 609 is coupled to the stem 606. A magnet 608 is coupled to the stem 606 by a spring 610, which may increase or dampen amplitude. An electromagnetic coil 612 is disposed inside the housing and capable of generating a magnetic field to attract or repel the magnet 608. A battery 614 and switch 616 are operatively coupled to the coil 612. In operation, the electromagnet periodically generates the magnetic field to axially oscillate the magnet 608. Movement of the magnet 608 is transferred to the stem 606 via the spring 610, thereby to move the second set of protrusions 609 relative to the first set of protrusions 607. The patterns and relative locations of the first and second sets of protrusions may vary, as illustrated in FIGS. 97A-C. In FIG. 97A, the first set includes one row 620 of stationary protrusions while the remaining protrusions move. Embodiments with three and four rows of stationary protrusions are illustrated in FIGS. 97B and 97C, respectively.

All documents cited in the Detailed Description are, in relevant part, incorporated herein by reference; the citation of any document is not to be construed as an admission that it is prior art with respect to the present disclosure.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this disclosure.

The invention claimed is:

1. A mascara applicator comprising:
   a handle;
   a stem defining a longitudinal stem axis and having a first end coupled to the handle and a second end;
   a mascara applicator head coupled to the stem second end and supported for movement relative to the handle in a direction substantially parallel to the stem axis; and
   an actuator operatively coupled to the applicator head for moving the applicator head in an axial motion comprising a forward stroke and a reverse stroke, wherein the forward stroke extends the applicator head away from the handle, and wherein the reverse stroke retracts the applicator head towards the handle; and a container comprising a mascara composition;
   wherein the applicator head comprises a major dimension oriented along the stem axis and a minor dimension oriented along a second axis perpendicular to the stem axis, and wherein the major dimension is greater than the minor dimension.

2. The applicator of claim 1, in which the axial motion comprises a displacement distance of approximately 0.1 to 10 mm.

3. The applicator of claim 1, in which axial motion comprises a frequency of approximately 0.5 to 1000 Hz.

4. The applicator of claim 1, in which the forward stroke comprises a forward stroke speed and the reverse stroke comprises a reverse stroke speed, wherein a ratio of the forward stroke speed to the reverse stroke speed is within a range of approximately 10:1 to 1:10.

5. The applicator of claim 1, in which the forward stroke is executed in a forward stroke time and the reverse stroke is executed in a reverse stroke time, wherein the axial motion further includes a pause period between the forward and reverse strokes of approximately 0.01% to 1000% of at least one time period selected from a group of time periods comprising the forward and reverse stroke times.

6. The apparatus of claim 1, in which the actuator comprises an electromagnetic coil.

7. The apparatus of claim 6, in which the electromagnetic coil is adapted to reciprocate a drive shaft in a linear direction, the apparatus further including a transmission coupling between the drive shaft and the applicator head for converting reciprocation of the drive shaft in the linear direction into the axial motion.

8. The apparatus of claim 6, in which the electromagnetic coil is adapted to generate a magnetic field, in which the apparatus further includes a magnet coupled to the applicator head and responsive to the magnetic field, and in which a power source is intermittently connected to the electromagnetic coil to actuate the applicator head in the axial motion.

9. The applicator of claim 1, in which the actuator comprises a motor having a rotating motor shaft, the apparatus further including a transmission coupling for automatically converting rotation of the motor shaft in one direction into axial movement of the applicator he d in both the forward and reverse strokes.

10. The apparatus of claim 1, in which the actuator further drives the applicator head in a rotational motion.

11. The apparatus of claim 1, in which the actuator further drives the applicator head in a vibrational motion.

12. A mascara applicator comprising
   a handle;
   a stem defining a longitude stem axis and having a first end coupled to the handle and a second end;
   a mascara applicator head coupled to the stem second end and supported for movement relative to the handle in a direction substantially parallel to the stem axis;
   a motor having a rotating motor shaft; and
   a transmission coupling disposed between the motor shaft and the applicator head for automatically converting rotation of the motor shaft in one direction into axial movement of the applicator head, the axial movement having a forward stroke and a reverse stroke; wherein the forward stroke extends the applicator head away from the handle, and wherein the reverse stroke retracts the applicator head towards the handle and a container comprising a mascara composition;
wherein the applicator head comprises a major dimension oriented along the stem axis and a minor dimension oriented along a second axis perpendicular to the stem axis, and wherein the major dimension is greater than the minor dimension.

13. The applicator of claim 12, in which the transmission coupling includes a stem disc coupled to the stem and a motor disc coupled to the motor shaft, wherein the motor disc engages the stem disc.

14. The applicator of claim 13, in which the motor disc is mounted eccentric to a motor shaft axis to provide a cam surface engaging the stem disc, wherein rotation of the motor disc drives the stem disc in an axial direction.

15. The apparatus of claim 13, in which the transmission coupling further includes a first cam surface coupled to the stem disc and a second cam surface coupled to the housing, and in which the motor disc frictionally engages and rotates the stem disc, wherein rotation of the first cam surface with respect to the second cam surface drives the stem disc in an axial direction.

16. The apparatus of claim 12, in which the applicator further comprises a spring.

* * * * *

UNITED STATES PATENT AND TRADEMARK OFFICE
CERTIFICATE OF CORRECTION

PATENT NO. : 7,654,271 B2 Page 1 of 1
APPLICATION NO. : 11/143525
DATED : February 2, 2010
INVENTOR(S) : Wyatt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 568 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO.        : 7,654,271 B2
APPLICATION NO.   : 11/143525
DATED             : February 2, 2010
INVENTOR(S)       : Peter Jonathan Wyatt et al.

Page 1 of 1

It is certified that error appears in the above-identified patent and that said Letters Patent is hereby corrected as shown below:

In the Claims

<u>Column 20</u>

Claim 3, line 11, after "which" insert -- the --.

Claim 9, line 43, delete "he d" and insert -- head --.

Claim 12, line 51, delete "longitude" and insert -- longitudinal --.

Signed and Sealed this
Fifth Day of May, 2015

Michelle K. Lee
*Director of the United States Patent and Trademark Office*